United States Patent
Wang et al.

(10) Patent No.: US 9,868,991 B2
(45) Date of Patent: Jan. 16, 2018

(54) NANOMOTORS AND MOTION-BASED DETECTION OF BIOMOLECULAR INTERACTIONS

(75) Inventors: Joseph Wang, San Diego, CA (US); Jie Wu, Nanjing (CN); Shankar Balasubramanian, Acton, MA (US); Daniel Kagan, Westfield, NJ (US); Kalayil Manian Manesh, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 506 days.

(21) Appl. No.: 13/637,645

(22) PCT Filed: Mar. 28, 2011

(86) PCT No.: PCT/US2011/030211
§ 371 (c)(1),
(2), (4) Date: Dec. 11, 2012

(87) PCT Pub. No.: WO2011/120048
PCT Pub. Date: Sep. 29, 2011

(65) Prior Publication Data
US 2013/0084569 A1   Apr. 4, 2013

Related U.S. Application Data

(60) Provisional application No. 61/317,963, filed on Mar. 26, 2010.

(51) Int. Cl.
B82Y 10/00 (2011.01)
C12Q 1/68 (2006.01)
(Continued)

(52) U.S. Cl.
CPC ............ *C12Q 1/6886* (2013.01); *C07K 17/14* (2013.01); *C12N 15/115* (2013.01);
(Continued)

(58) Field of Classification Search
None
See application file for complete search history.

(56) References Cited

U.S. PATENT DOCUMENTS 3,363,983 A   1/1968  Roberts
7,087,148 B1  8/2006  Blackburn
(Continued)

FOREIGN PATENT DOCUMENTS

WO   2003099112   12/2003
WO   2011031463    3/2011

OTHER PUBLICATIONS

Carpini et al. Biosensors and Bioelectronics. 2004 20: 167-175.*
(Continued)

*Primary Examiner* — Joseph G. Dauner
(74) *Attorney, Agent, or Firm* — Perkins Coie LLP

(57) ABSTRACT

Techniques and systems are disclosed for detecting biomolecular interactions based on the motion of nanomotors. In one aspect, a method of detecting biomolecular interactions based on a motion of a nanomachine includes functionalizing a nanomachine with a capture probe adapted to interact with biological targets; and detecting a presence of the biological targets in an environment based on a motion of the nanomachine.

19 Claims, 20 Drawing Sheets

(51) Int. Cl.
| | |
|---|---|
| G01N 33/557 | (2006.01) |
| G01N 33/58 | (2006.01) |
| C07K 17/14 | (2006.01) |
| C12N 15/115 | (2010.01) |
| G01N 33/558 | (2006.01) |
| B82Y 15/00 | (2011.01) |

(52) U.S. Cl.
CPC ......... *C12Q 1/6816* (2013.01); *G01N 33/557* (2013.01); *G01N 33/558* (2013.01); *G01N 33/587* (2013.01); *B82Y 15/00* (2013.01); *Y10S 977/726* (2013.01); *Y10S 977/773* (2013.01); *Y10S 977/92* (2013.01)

(56) References Cited

U.S. PATENT DOCUMENTS

| | | | |
|---|---|---|---|
| 7,347,974 | B1 | 3/2008 | Snow et al. |
| 7,357,018 | B2 | 4/2008 | Curry et al. |
| 7,516,759 | B2 | 4/2009 | Paxton et al. |
| 2002/0146745 | A1* | 10/2002 | Natan et al. .................. 435/7.1 |
| 2002/0192722 | A1 | 12/2002 | Stolowitz et al. |
| 2004/0158051 | A1 | 8/2004 | Ozkan |
| 2004/0209376 | A1* | 10/2004 | Natan et al. .................. 436/56 |
| 2005/0123937 | A1 | 6/2005 | Thorp et al. |
| 2005/0164402 | A1 | 7/2005 | Belisle |
| 2005/0176029 | A1* | 8/2005 | Heller et al. .................. 435/6 |
| 2005/0266416 | A1 | 12/2005 | Guo |
| 2007/0105119 | A1 | 5/2007 | Gao et al. |
| 2008/0156654 | A1 | 7/2008 | Wang et al. |
| 2008/0187764 | A1 | 8/2008 | Jung et al. |
| 2009/0212275 | A1 | 8/2009 | Park et al. |
| 2010/0129656 | A1 | 5/2010 | Zussman et al. |
| 2010/0276302 | A1 | 11/2010 | Raguse |

OTHER PUBLICATIONS

"Transducer" definition from dictionary.com. Retrieved on Oct. 4, 2016 from the internet: http://www.dictionary.com/browse/transducer.*
Adhikari, B. et al., "Polymers in sensor applications", Progress in Polymer Science, 2004, vol. 29, pp. 699-766.
Alon, U. et al., "Robustness in bacterial chemotaxis", Nature, 1999, vol. 397, pp. 168-171.
Anderson, J., "Colloid Transport by Interfacial Forces", Annu. Rev. Fluid Mec. 1989, vol. 21, pp. 61-99.
Balasubramanian, S, et al., "Thermal Modulation of Nanomotor Movement," *Small*, 5(13):1569-1574, Mar. 2009.
Beckmann, A. et al., "Modeling Hot Wire Electrochemistry. Coupled Heat and Mass Transport at a Directly and Continuously Heated Wire", J. Phys. Chem B 2000, 104, pp. 764-769.
Behkam, B. et al., "Bacterial Flagella-Based Propulsion and On/Off Motion Control of Microscale Objects", Appl. Phys. Lett. 2007, 90, 023902.
Berg, H.C. et al., "The Rotary Motor of Bacterial Flagella", Annu. Rev. Biochem. 2003, 72, pp. 19-54.
Burdick, J., et al., "Synthetic Nanomotors in Microchannel Networks: Directional Microchip Motion and Controlled Manipulation of Cargo," *Journal of the American Chemical Society*, 130(26):8164-8165, Jun. 2008.
Byun, S. C., Authorized Officer, Korean Intellectual Property Office, Interntational Search Report and Written Opinion, PCT Application No. PCT/US2012/000029, dated Nov. 23, 2012, 10 pages.
Calvo-Marzal, P., et al., "Electrochemically-triggered motion of catalytic nanomotors," *The Royal Society of Chemistry: Chemical Communications*, 14(30):4509-4511, Jun. 2009.
Campuzano, S. et al., "Bacterial Isolation by Lectin-Modified Microengines", Nano Lett. 12, 2012, 396-401.
Cao, Y. W. C., Jin, R. C. & Mirkin, C. A. Nanoparticles with Raman spectroscopic fingerprints for DNA and RNA detection. Science 297, 1536-1540 (2002).

Cartwright, J., "Nanomotors detect trace silver," *Royal Society of Chemistry*, published Aug. 14, 2009, obtained online Apr. 2015 <http://www.rsc.org/chemistryworld/News/2009/August/14080901.asp>.
Catchmark, J. M., et al., "Directed Rotational Motion of Microscale Objects Using Interfacial Tension Gradients continually Generated via Catalytic Reactions", Small 2005, 1, No. 2, pp. 202-206.
Chang, T. S. et al., "Remotely powered self-propelling particles and micropumps based on miniature diodes", Nature Mat. 2007, vol. 6, pp. 235-240.
Choi, J. W., Authorized Officer, Korean Intellectual Property Office, Interntational Search Report and Written Opinion, PCT Application No. PCT/US2012/023410, dated Sep. 21, 2012, 9 pages.
Choi, S., Authorized Officer, Korean Intellectual Property Office, Interntational Search Report and Written Opinion, PCT Application No. PCT/US2011/053783, dated May 4, 2012, 8 pages.
Demirok, U.K., et al., "Ultrafast Catalytic Alloy Nanomotors," *Angewandte Chemie International Edition*, 47(48):9349-9351, Oct. 2008.
Fischer, T., Agarwal, A. & Hess, H. "A smart dust biosensor powered by kinesin motors", Nature Nanotech. 4, 2009, pp. 162-166.
Flechsig, G. -U. et al., Investigation of Deposition and Stripping Phenomena at the Heated Gold Wire Electrode in Comparison to the Rotating Disk Electrode: Copper(II), Mercury(II), and Arsenic(III), Electroanalysis 2001, 13, 786.
Fournier-Bidoz, S. et al., "Synthetic self-propelled nanorotors", Chem. Commun. 2005, pp. 441-443.
Frischmuth, K. et al., "On Modelling Heat Transfer in Chemical Microsensors", Int. J. Eng. Sci. vol. 34, No. 5, pp. 523-530.
Gao, W. et al., "Highly Efficient Catalytic Microengines: Template Electrosynthesis of Polyaniline/Platinum Microtubes", J. Am. Chem. Soc., Jul. 2011, vol. 133, No. 31, pp. 11862-11864.
Gao, W. et al., "Magnetically Powered Flexible Metal Nanowire Motors", J. Am. Chem. Soc., 2010, 132, pp. 14403-14405.
Ghosh, A. et al., "Controlled Propulsion of Artificial Magnetic Nanostructured Propellers", Nano Lett. 2009, vol. 9, No. 6, pp. 2243-2245.
Gibbs, J. G. et al., "Autonomously motile catalytic nanomotors by bubble propulsion", Appl. Phys. Lett. 2009, 94, 163104.
Gibbs, J. G. et al., "Design and Characterization of Rotational Multicomponents Catalytic Nanomotors", Small 2009, 5, No. 20, pp. 2304-2308.
Goel, A. et al., "Harnessing biological motors to engineer systems for nanoscale transport and assembly", Nature Nanotechnology 2008, vol. 3, pp. 465-475.
Gooding, J.J., "Electrochemical DNA hybridization biosensors", Electroanalysis 2002, 14, No. 17, pp. 1149-1156.
Goszner K. et al., "The Decomposition of Hydrogen Peroxide on Silver-Gold Alloys", J. Catal. 32, 1974, pp. 175-182.
Gründler, P. et al., Hot-wire Electrodes: Voltammetry Above the Boiling Point, Analyst, 1996, vol. 121, pp. 1805-1810.
Gründler, P. et al., "The Technology of Hot-Wire Electrochemistry", Electroanalysis 1999, 11, No. 4, pp. 223-228.
Gründler, P. et al., "Principles and Analytical Applications of Heated Electrodes", Microchim. Acta 154, 2006, pp. 175-189.
Hall, S.B. et al., "Electrochemical oxidation of hydrogen peroxide at platinum electrodes. Part III: Effect of temperature", Electrochim. Acta 44, 1999, pp. 2455-2462.
He, Y. et al., "Designing Catalytic Nanomotors by Dynamic Shadowing Growth", Nano Left. 2007, vol. 7, No. 5, 1369-1375.
Herr, J.K. et al., "Aptamer-conjugated nanoparticles for selective collection and detection of cancer cells", Anal. Chem. 2006, 78, pp. 2918-2924.
Hess, H. et al., "Light-Controlled Molecular Shuttles Made from Motor Proteins Carrying Cargo on engineered Surfaces", Nano. Letters, 2001, vol. 1, No. 5, pp. 235-239.
Hess, H. et al., "Biomolecular motors", nanotoday, 2005, pp. 22-29.
Hianik, T. et al., "Influence of ionic strength, pH and aptamer configuration for binding affinity to thrombin" Bioelectrochemistry 70, 2007, pp. 127-133.

(56) References Cited

OTHER PUBLICATIONS

Hill, H.D. et al., "The bio-barcode assay for the detection of protein and nucleic acid targets using DTT-induced ligand exchange" Nature Protocols 1, 2006, pp. 324-336.
Honda et al., "Electrochemical Behavior of $H_2O_2$ AT Ag In $HClO_4$ Aqueous Solution", Electrochim. Acta, vol. 31, No. 3, 1986, pp. 377-383.
Hong, S. R., Authorized Officer, Korean Intellectual Property Office, Interntational Search Report and Written Opinion, PCT Application No. PCT/US2013/026757, dated Jul. 25, 2013, 14 pages.
Hong, Y. et al., "Chemotaxis of Nonbiological Colloidol Rods", Phys. Rev. Lett. 2007, 99, 178103.
Howse, J. R. et al., "Self-Motile Colloidal Particles: From Directed Propulsion to Random Walk", Phys. Rev. Lett 2007, 99, 048102.
Huang, S. L. et al., "Acoustically active liposomes for drug encapsulation and ultrasound-triggered release", Biochimia et Biophysica Acta., Aug. 12, 2004, vol. 1665, pp. 134-141.
Ibele, M. et al., "Schooling Behavior of Light-Powered Autonomous Micromotors in Water", Angew. Chem. Int. Ed. 2009, 48, pp. 3308-3312.
Ibsen, S. et al., "A Novel Nested Liposome Drug Delivery Vehicle Capable of Ultrasound Triggered Release of its Payload", J Control Release, Nov. 7, 2011, vol. 155, No. 3, pp. 358-366.
Park, Jong Chul, Authorized Officer, Korean Intellectual Property Office, International Search Report and Written Opinion dated Jun. 3, 2011 for International Application No. PCT/US2010/046558, 8 pages.
Ismagilov, R. F. et al., "Autonomous Movement and Self-Assembly", Angew. Chem. Int. Ed. 2002, 41, No. 4, pp. 652-654.
Kagan, D., et al., "Chemical Sensing Based on Catalytic Nanomotors: Motion-Based Detection of Trace Silver, " *Journal of the American Chemical Society*, Aug. 2009, 131(34):12082-12083.
Keating, C.D. et al., "Striped metal nanowires as building blocks and optical tags", Adv. Materials, 2003, 15, pp. 451-454.
Klibanov, A. L. et al., "Ultrasound-triggered release of materials entrapped in microbubble-liposome constructs: a tool for targeted drug delivery", J Control Release, Nov. 20, 2010, vol. 148, No. 1, pp. 13-17.
Kline, T. R. et al., "Catalytic nanomotors: remote-controlled autonomous movement of striped metallic nanorods", Angew. Chem. Int., 2005, Ed 44, pp. 744-746.
Lahav, M. et al., "Core-Shell and Segmented Polymer-Metal Composite Nanostructures", Nano Letters, 2006, vol. 6, No. 9, pp. 2166-2171.
Laocharoensuk, R., et al., "Carbon-Nanotube-Induced Acceleration of Catalytic Nanomotors," *ACS Nano*, 2008, 2(5):1069-1075.
Lee, D.-W., Authorized Officer, Korean Intellectual Property Office, Interntational Search Report and Written Opinion, PCT Application No. PCT/US2011/030211, dated Jan. 2, 2012, 8 pages.
Lee, J. S. et al., "Silver Nanoparticle-oligonucleotide conjugates based on DNA with triple cyclic disulfide moieties", Nano Letters 2007, 7, pp. 2112-2115.
Liao, J. C. et al., "Use of electrochemical DNA biosensors for rapid molecular identification of uropathogens in clinical urine specimens", J. Clin. Microbiol., 2006, 44, pp. 561-570.
Liu, W., et al., "Enzymatically Synthesized Conducting Polyaniline," *Journal of the American Chemical Society*, 1998, 121(1):71-78.
Luo, X., et al., "Enzymatic Nanolithography of Polyaniline Nanopatterns by Using Peroxidase-Modified Atomic Force Microscopy Tips," *Chemistry—A European Journal*, 2009, 15(21):5191-5194.
Manesh, K. et al., "Motion control at the nanoscale", Small 2010, 6, pp. 338-345.
Manesh, K. M., et al., "Nanomotor-based writing of surface microstructures," *The Royal Society of Chemistry: Chemical Communications*, 2010, 46(31):5704-5706.
Mano, N. et al., "Bioelectrichemical Propulsion", J. Am. Chem. Soc. 2005, 127, pp. 11574-11575.
Mascaro, L.H. et al., "Underpotential deposition of silver on polycrystalline platinum studied by cyclic voltammetry and rotating ring-disc techniques", J. Chem. Soc., Faraday Trans., 1997, 93(22), pp. 3999-4003.
Mei, Y. et al., "Versatile Approach for Integrative and Functionalized Tubes by Strain Engineering of Nanomembranes on Polymers", Adv. Mater., Oct. 15, 2008, vol. 20, No. 21, pp. 4085-4090.
Mihajlovic, G. et al., "All-electrical switching and control mechanism for actomyosin-powered nanoactuators", Appl. Physics Left. 2004, 85, 1060.
Mirkovic, T. et al., "Nanolocomotion: catalytic nanomotors and nanorotors", Small 2010, 6, No. 2, 159-167.
Miyamoto, Y. et al., "Direct Inhibition of Microtubule-Based Kinesin Motility by Local Anesthetics", Biophys. J. 2000, 78, pp. 940-949.
Niidome, Y. et al., "Characterization of silver ions adsorbed on gold nanorods: surface analysis by using surface-assisted laser desorption/ionization time-of-flight mass spectrometry", Chem. Commun, 2009, pp. 1754-1756.
Okahata, Y. et al., "Hybridization of nucleic-acids immobilized on a quartz crystal microbalance", J. Am. Chem. Soc., 1992, 114, pp. 8299-8300.
Orendorff, C. J. et al., "Quantitation of Metal Content in the Silver-Assisted Growth of Gold Nanorods", J. Phys. Chem. B, 2006, 110, pp. 3990-3994.
Orozco, J. et al., "Dynamic Isolation and Unloading of Target Proteins by Aptamer-Modified Microtransporters", Anal. Chem., 83, 2011, pp. 7962-7969.
Ozin, G.A., et al., "Dream Nanomachines," *Advanced Materials*, Dec. 2005, 17(24):3011- 3018.
Pal, S., et al., "Stable silver nanoparticle-DNA conjugates for directed self-assembly of core-satellite silver-gold nanoclusters", Chem. Commun., 2009, 40, pp. 6059-6061.
Palecek, E. et al., "Detecting DNA hybridization and damage", Anal. Chem. 2001, 73, pp. 74A-83A.
Parsons et al., "The oxidation of small organic molecules", J. Electroanal. Chem., 1988, 257, pp. 9-45.
Paxton, W. F. et al., "Catalytically Induced Electrokinetics for Motors and Micropumps", J. Am. Chem. Soc. 2006, 128, pp. 14881-14888.
Paxton et al., "Chemical Locomotion", Angew. Chemie. Int. Ed. 2006, 45, pp. 5420-5429.
Paxton, W.F. et al., "Motility of Catalytic Nanoparticles through Self-Generated Forces", Chem. Eur. J. 2005, 11, pp. 6462-6470.
Paxton, W.F. et al., "Catalytic Nanomotors: Autonomous Movement of Striped Nanorods", J. Am Chem. Soc. 2004, 126, pp. 13424-13431.
Piner, R.D., et al., "'Dip-Pen Nanolithography", *Science*, 1999, 283(5402):661-663.
Piunno, P. A. E. et al., "Fiber optic DNA sensor for fluorometric nuclei acid determination", Anal. Chem. 1995, 67, pp. 2635-2643.
Prieve, D. C., "Changes in zeta potential caused by a dc electric current for thin double layers", Colloids Surf. A: Physicochem. Eng. Aspects, 2004, 250, pp. 67-77.
Rosi, N. L. et al., "Nanostructures in biodiagnostics", Chem. Rev. 2005, 105, pp. 1547-1562.
Salaita, K., et al., "Applications of dip-pen nanolithography," *Nature Nanotechnology*, Feb. 2007, 2(3):145-155.
Solovev, A. A. et al., "Catalytic Microtubular Jet Engines Self-Propelled by Accumulated Gas Bubbles, Small, Jul. 17 2009, vol. 5, No. 14, pp. 1688-1692.
Strohmeier, R. et al., "Control of Cell Shape and Locomotion by External Calcium", Exp. Cell Res. 1984, 154, pp. 412-420.
Sundararajan, S., et al., "Catalytic Motors for Transport of Colloidal Cargo", Apr. 2008, *Nano Letters*, 8(5):1271-1276.
Suwansa-Ard, S. et al., "Prussian blue dispersed sphere catalytic labels for amplified electronic detection of DNA", Electroanalysis, 2008, 20, pp. 308-312.
Takeda, S., et al., "Lithographing of Biomolecules on a Substrate Surface Using an Enzyme-Immobilized AFM Tip," *Nano Letters*, Oct. 2003, 3(11):1471-1474.
Taton, T. A. et al., "Scanometric DNA Array Detection with Nanoparticle Probes", Science 2000, 289, pp. 1757-1759.

(56) References Cited

OTHER PUBLICATIONS

Thompson, D. G. et al., "Ultrasensitive DNA detection using oligonucleotide-silver nanoparticle conjugates", Anal. Chem., 2008, 80, 2805-2810 (2008).
Tokareva, I. et al., "Hybridization of oligonucleotide-modified silver and gold nanoparticles in aqueous dispersions and on gold films", J. Am. Chem. Soc. 2004, 126, pp. 15784-15789.
Tseng, A. A. et al., Nanofabrication by scanning probe microscope lithography: A review, J. Vac. Sci. Technol., 2005, B, 23, pp. 877-894.
Van Den Heuvel, M.G.L et al., "Motor Proteins at Work for Nanotechnology", Science 2007, 317, pp. 333-336.
Wachholz, F. et al., "Temperature pulse modulated amperometry at compact electrochemical sensors", Electrochem. Commun. 2007, 9, pp. 2346-2352.
Wang, J., "From DNA biosensors to gene chips", Nucl. Acids Res., 2000, 28, pp. 3011-3016.
Wang, J. et al., "Motion Control at the Nanoscale", Small, 2010, 6, No. 3, pp. 338-345.
Wang, J., "Nanomaterial-based amplified transduction of biomolecular interactions", Small 2005, 1, pp. 1036-1043.
Wang, J., "Can man-made nanomachines compete with nature biomotors?" *ACS Nano*, Jan. 2009, 3(1):4-9.
Wang, J. et al., "Silver-enhanced colloidal gold electrochemical stripping detection of DNA hybridization", Langmuir 2001, 17, pp. 5739-5741.
Wang, Y. et al., "Bipolar Electrochemical Mechanism for the Propulsion of Catalytic Nanomotors in Hydrogen Peroxide Solutions", Langmuir 2006, 22, pp. 10451-10456.
Watanabe, M. et al., "Electronic detection of DNA mutation based on strand exchange reaction", Biorg. Medicinal Chemistry, 2009, 17, pp. 1494-1497.
Whitesides, G.M., "The Once and Future Nanomachine," *Scientific American*, Sep. 2001, 285(3):70-75.
Wildgoose, G.G. et al., "High-Temperature Electrochemistry: A Review", Electroanalysis 2004, 16, No. 16, pp. 421-432.
Wouters, D., et al., "Nanolithography and Nanochemistry: Probe-Related Patterning Techniques and Chemical Modification for Nanometer-Sized Devices," *Angewandte Chemie International Edition*, May 2004, 43(19):2480-2495.
Yamazaki, S. et al., "A fuel cell with selective electrocatalysts using hydrogen peroxide as both an electron acceptor and a fuel", J. Power Sources 2008, 178, pp. 20-25.
York, J. et al., "Single-molecule detection of DNA via sequence-specific links between F1-ATPase motors and gold nanorod sensors", Lab on Chip 8, 2008, pp. 415-419.
Zacharia, N. S. et al., "Enhanced speed of bimetallic nanorod motors by surface roughening", Chem. Commun., 2009, pp. 5856-5858.
Zerihun, T. et al., "Oxidation of formaldehyde, methanol, formic acid and glucose at ac heated cylindrical Pt microelectrodes", J. Electroanal. Chem. 1998, 441, pp. 57-63.
Zhang, L. et al., "Artificial bacterial flagella: Fabrication and magnetic control", Appl. Phys. Lett. 2009, 94, 064107.
Zhang, L. et al., "Controlled propulsion and cargo transport of rotating nick el nanowires near a patterned solid surface, ACS Nano vol. 4, No. 10, pp. 6228-6234.
Arya, S.K.et al., "Recent advances in self-assembled monolayers based biomolecular electronic devices", Biosens. Bioelectron. 24, 2009, pp. 2810-2817.
Batchelor-Mcauley, C. et al., "The physicochemical aspects of DNA sensing using electrochemical methods", Biosens. Bioelectron. 24, 2009, pp. 3183-3190.
Campuzano, J.C. et al., "Photoemission in the High Tc Superconductors", Sep. 19, 2002, 109 pages.
Campuzano, S. et al., "Ternary monolayers as DNA recognition interfaces for direct and sensitive electrochemical detection in untreated clnical samples", Biosensors and Bioelectronics, Feb. 2011, vol. 26, pp. 3577-3583.

Chumbimuni-Torres, K.Y. et al., "Amplified potentiometric transduction of DNA hybridization using ion-loaded liposomes", Analyst, 2010, 135, pp. 1618-1623.
Das, J. et al., ,,Ultrasensitive Detection of DNA in Diluted Serum Using NaBH4 Electrooxidation Mediated by [Ru(NH3)6]3+ at Indium-Tin Oxide Electrodes, Langmuir 2010, 26(9), pp. 6804-6808.
Dharuman, V. et al., "Ternary mixed monolayers for simultaneous DNA orientation control and surface passivation for label free DNA hybridization electrochemical sensing", Biosensors and Bioelectomics, 2010, vol. 25, pp. 2129-2134.
Harpster, M. H. et al., SERS detection of indirect viral DNA capture using colloidal gold and methylene blue as a Raman label, Biosensors and Bioelectronics, 2009, vol. 25, pp. 674-681.
Janek, R. P. et al., "Impedance Spectroscopy of Self-Assembled Monolayers on Au(111): Sodium Ferrocyanide Charge Transfer at Modified Electrodes", Langmuir 1998, 14, pp. 3011-3018.
Keighley, S. D. et al., "Optimization of label-free DNA detection with electrochemical impedance spectroscopy using PNA probes", Biosensors and Bioelectronics 24, 2008, pp. 906-911.
Kim, Y.-K., Authorized Officer, Korean Intellectual Property Office, International Search Report, International Application No. PCT/US2012/023039, dated Nov. 20, 2012.
Kuralay, F. et al., "Highly sensitive disposable nucleic acid biosensors for direct bioelectronics detection in raw biological samples", Talanta, Jun. 2011, vol. 85, pp. 1330-1337.
Levicky, R. et al., "Using Self-Assembly to Control the Structure of DNA Monolayers on Gold: A Neutron Reflectivity Study", J. Am. Chem. Soc., 1998, 120, pp. 9787-9792.
Liao, J.C. et al., "Development of an Advanced Electrochemical DNA Biosensor for Bacterial Pathogen Detection", J. Mol. Diagn. vol. 9, No. 2, Apr. 2007, pp. 158-168.
Luong, J. H.T. et al., "Biosensor technology: Technology push versus market pull", Biotechnology Advances 26 (2008) pp. 492-500.
Miranda-Castro, R. et al., "Structured Nucleic Acid Probes for Electrochemical Devices", Electroanalysis 2009, 21, No. 19, pp. 2077-2090.
Park, S.-M. et al., "Electrochemical Impedance Spectroscopy for Better Electrochemical Measurements", Analytical Chemistry, Nov. 1, 2003, pp. 455-461.
Patterson, A. et al., "Using Triplex-Forming Oligonucleotide Probes for the Reagentless, Electrochemical Detection of Double-Stranded DNA", Anal. Chem. 2010, 82, pp. 9109-9115.
Piela, B. et al., "Capacitance of the gold electrode in 0.5 M H2SO4 solution: a.c. impedance studies", Journal of Electroanalytical Chemistry 388 (1995) pp. 69-79.
Sadik, O.A. et al., "Status of biomolecular recognition using electrochemical techniques", Biosens. Bioelectron. 24, 2009, pp. 2749-2765.
Sassolas, A. et al., "DNA Biosensors and Microarrays", Chem. Rev. 2008, 108, pp. 109-139.
Seifert, M. et al., Characterization of streptavidin binding to biotinylated, binary self assembled thiol monolayers-influence of component ration and solvent, Langmuir, 2010, vol. 26, No. 9, pp. 6386-6393.
Steel, G. J. et al., "A Screen for Dominant Negative Mutants of SEC18 Reveals a Role for the AAA Protein Consensus Sequence in ATP Hydrolysis", Molecular Biology of the Cell, vol. 11, Apr. 2000, pp. 1345-1356.
Steel, M. et al., "Gene-Trapping to Identify and Analyze Genes Expressed in the Mouse Hippocampus", Hippocampus 8, 1998, pp. 444-457.
Tosar, J.P. et al., "Electrochemical DNA hybridization sensors applied to real and complex biological samples", Biosens. Bioelectron. 26, 2010, pp. 1205-1217.
Wang, J., "Electrochemical biosensors: Towards point-of-care cancer diagnostics", Biosens. Bioelectron. 21, 2006, pp. 1887-1892.
Wu, Beili et al., "Structures of the CXCR4 Chemokine GPCR with Small-Molecule and Cyclic Peptide Antagonists", Science, 2010, vol. 330, pp. 1066-1071.

(56) References Cited

OTHER PUBLICATIONS

Wu, J. et al., "Ternary Surface monolayers for Ultrasensitive (Zeptomole) Amperometric Detection of Nucleic Acid Hybridization without Signature Amplification", Anal. Chem., 2010, 82, pp. 8830-8837.

Zhang, J. et al., "Design of an Oligonucleotide-Incorporated Nonfouling Surface and Its Application in Electrochemica DNA Sensors for Highly Sensitive and Sequence-Specific Detection of Target DNA", Anal. Chem. 2008, 80, pp. 9029-9033.

Wu et al., "Potentiometric Detection of DNA Hybridization using Enzyme-Induced Metallization and a Silver Ion Selective Electrode," Analytical Chemistry, vol. 81, No. 24, Dec. 15, 2009, pp. 1007-1012.

Ferguson, J. A., Boles, T. C., Adams, C. P. & Walt, D. R. "A fiber-optic DNA biosensor microarray for the analysis of gene expression,." Nat. Biotechnol. 14, 1681-1684 (1996).

Mallouk, T. E. & Sen, A. "Powering nanorobots." Sci. Amer. 300, 72-77 (2009).

Clemmens, J. et al., "Analysis of Microtubule Guidance in Open Microfabricated Channels Coated with the Motor Protein Kinesin", Langmuir 2003, 19, pp. 1738-1744.

Dharuman, V. et al., "Label free electrochemical DNA hybridization discrimination effects at the binary and ternary mixed monolayers of single stranded DNA/diluent/s in presence of cationic intercalators", Biosens. Bioelectron, 23, 2008, pp. 1250-1258.

Gründler, P. et al., "Deposition and stripping at heated microelectrodes. Arsenic(V) at a gold electrode", Electrochim. Acta, 1998, vol. 43, pp. 3451-3458.

Qin, L. et al., "Rational design and Synthesis of Catalutically Driven Nanorotors", J. Am. Chem. Soc. 2007, 129, pp. 14870-14871.

Walter, F.P. et al., "Catalytic Nanomotors: Autonomous Movement of Striped Nanorods", J. Am. Chem. Soc. 126, 2004, pp. 13424-13431.

Wang, Y. et al., "Dynamic Interactions between Fast Microscale Rotors", Am. Chem. Soc. 2009, 131, pp. 9926-9927.

Yamaguchi, et al., "Thermally Responsive Supramolecular Nanomeshes for On/Off Switching of the Rotary Motion of F1-ATPase at the Single-Molecule Level", Chem. Eur. J. 2008, 14, pp. 1891-1896.

Hess, et al., "Powering Nanodevices with Biomolecular Motors", Chem. Eur. J. 2004, 10, pp. 2110-2116.

Soong, R.K., et al., "Powering an Inorganic Nanodevice with a Biomolecular Motor", Science, 2000, vol. 290, pp. 1555-1558.

Neidhardt, F., et al., Chemical composition of *Escherichia coli*, p. 13-16 in F. Neidhardt et al. (ed.), *Escherichia coli* and *Salmonella typhimurium*, 2nd ed., vol. I. ASM Press, Washington, D.C. (1996).

Adler, J., "Chemotaxis in Bacteria", Science 2006, vol. 153, pp. 708-716.

\* cited by examiner

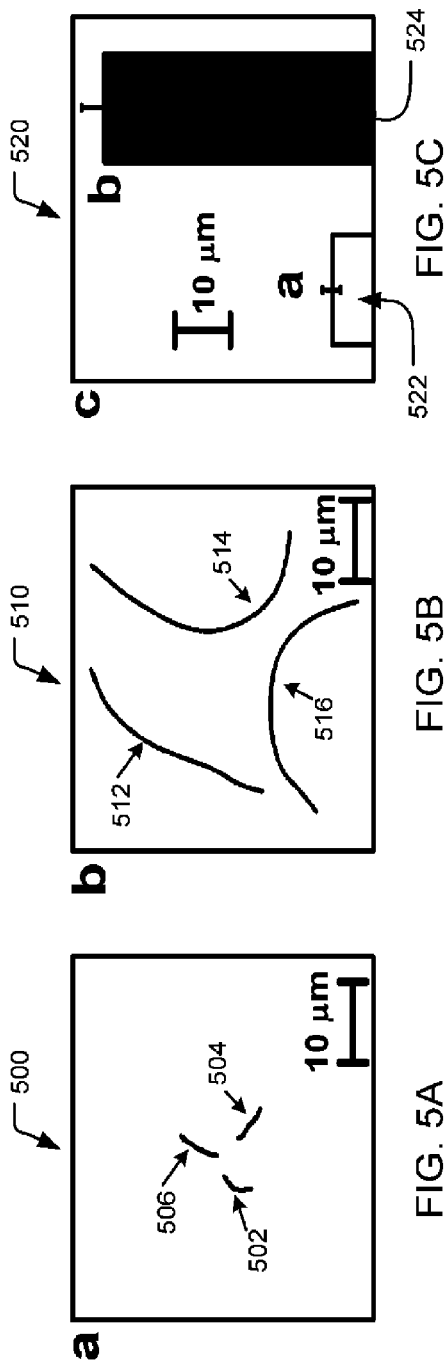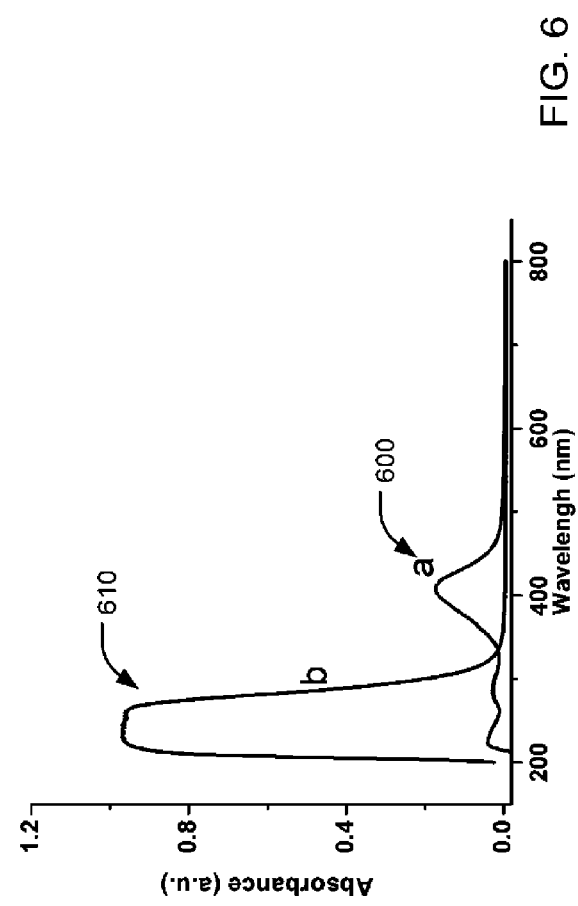

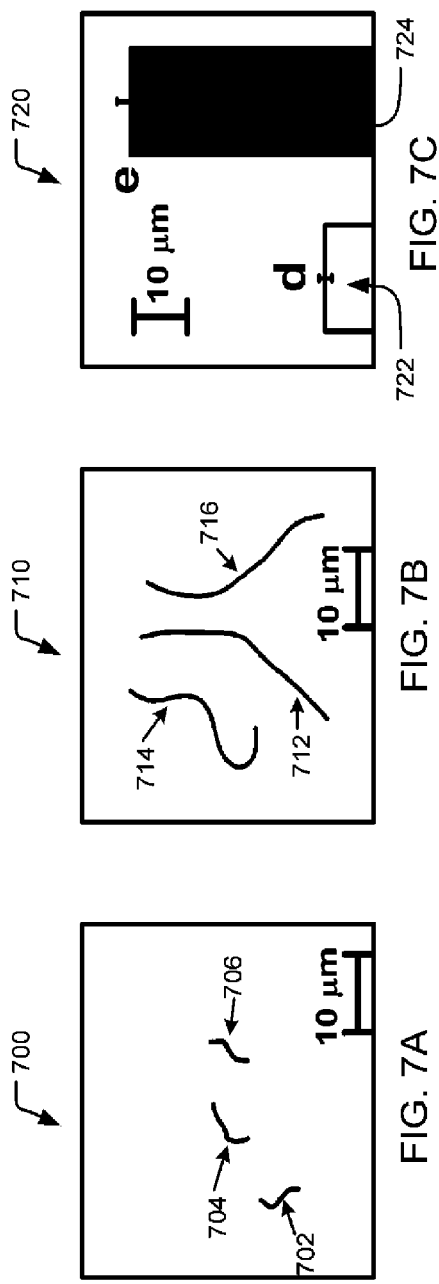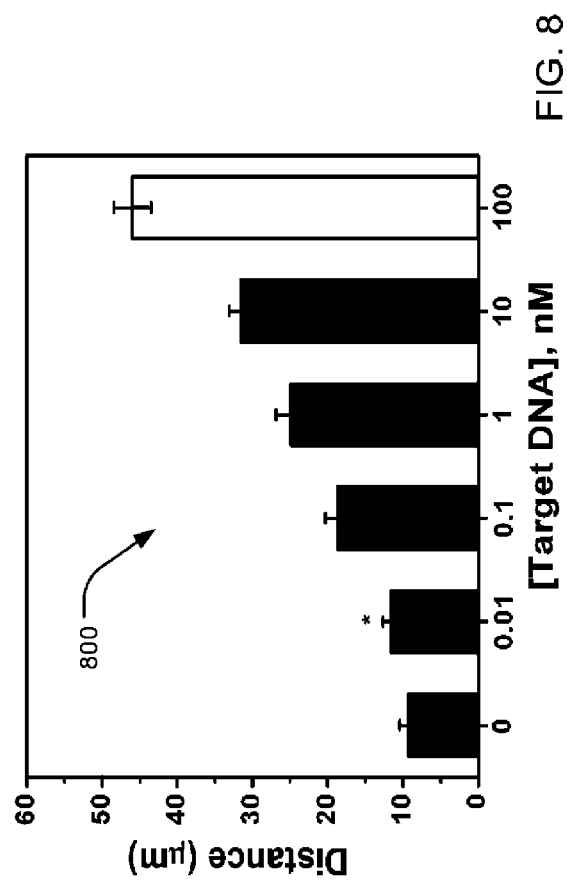

NANOMOTORS AND MOTION-BASED DETECTION OF BIOMOLECULAR INTERACTIONS

PRIORITY CLAIM AND RELATED APPLICATION

This application claims the priority of U.S. Provisional Application No. 61/317,963 entitled "NANOMOTORS AND MOTION-BASED DETECTION OF BIOMOLECULAR INTERACTIONS" and filed on Mar. 26, 2010, the entire disclosure of which is incorporated by reference as part of this application.

STATEMENT REGARDING FEDERAL RIGHTS

This invention was made with government support under grant no. CHE0840684 awarded by the National Science Foundation. The government has certain rights in the invention.

BACKGROUND

This application relates to devices and techniques that use nanomotors.

DNA hybridization biosensors used in wide-scale genetic testing commonly rely on different types of optical, electrochemical and mechanical transducers to convert duplex formation recognition events into useful analytical signals. Nanomaterial tags can be beneficial for such bioassays through amplified or multiplexed measurements. Synthetic nanomotors, converting chemical energy into autonomous motion can have various applications. Characteristics of synthetic nanomotors can include force, speed, efficiency, versatility, and motion control.

SUMMARY

Techniques and structures and apparatus are disclosed for implementing recognition-induced motion of artificial nanomotors and displacement-driven, tag-induced motility for biodetection.

In one aspect, a method of detecting biomolecular interactions based on a motion of a nanomachine includes functionalizing a nanomachine with a capture probe adapted to interact with biological targets. The method includes detecting a presence of the biological targets in an environment based on a motion of the nanomachine.

Implementations can optionally include one or more of the following limitations. Detecting the presence of the biological targets can include detecting a concentration of the biological targets based on a distance traveled by the functionalized nanomachine. Detecting the presence of the biological targets in an environment can include providing the functionalized nanomachine and nanoparticle tags in the environment to allow the capture probe to form a complex with the nanoparticle tags and the biological targets; and detecting the complex formation based on the motion of the functionalized nanomachine. Detecting the complex formation can include detecting the motion of the functionalized nanomachine in a nanoparticle-releasing solution. The presence of the released nanoparticle speeds up the motion of the functionalized nanomachine. The method of claim 1, wherein the nanoparticle tags comprise silver nanoparticle tags. The nanomachine can include an anode segment and a cathode segment. The anode segment can include platinum and the cathode can include gold. The biological targets can include nucleic acid targets. The method can include applying an external stimulus to control the motion of the nanomachine. The external stimulus can include at least one of electromagnetic, thermal or electrochemical pulses. The biological targets can include cancer biomarkers.

In another aspect, a device for detecting biomolecular interactions, the device includes a nanomachine functionalized with a capture probe adapted to interact with biological targets. The functionalized nanomachine is adapted to detect a presence of the biological targets in an environment based on a motion of the nanomachine.

Implementations can optionally include one or more of the following features. The functionalized nanomachine can be configured to detect a concentration of the biological targets based on a distance traveled by the functionalized nanomachine. The capture probe can be adapted to form a complex with the nanoparticle tags and the biological targets, and the complex formation can be confirmed based on the motion of the functionalized nanomachine. The functionalized nanomachine can be adapted to move in a nanoparticle-releasing solution. The presence of the released nanoparticle speeds up the motion of the functionalized nanomachine. The nanoparticle tags can include silver nanoparticle tags. The nanomachine can include an anode segment and a cathode segment. The anode segment can include platinum and the cathode can include gold. The biological targets can include nucleic acid targets. The biological targets can include cancer biomarkers.

The subject matter described in this specification potentially can provide one or more of the following advantages. For example, a relationship between the distance traveled by the nanowire (or nanomachine) and the concentration of the biological target can allow for 1) detection of the biological target of interest; and 2) determination of the concentration of the biological target based on visual inspection of the motion of the nanowire. Also, the instantaneous dissolution of metal nanoparticles in the fuel solution and the resulting silver-induced accelerated motion can be used to detect nucleic-acid hybridization.

BRIEF DESCRIPTION OF THE DRAWINGS

FIGS. 5A, 5B and 5C show silver nanoparticle (Ag NP) tag-induced nanomotor acceleration.

FIG. 6 shows UV-Vis spectroscopy spectra data confirming instantaneous dissolution of Ag NPs in peroxide fuel.

FIGS. 7A, 7B and 7C show Ag NP tag-induced nanomotor acceleration after complete hybridization assays.

FIG. 8 is a column graph 800 showing motion based DNA detection using nanomotor (Au—Pt) distance relationship with target DNA concentration in 15% $H_2O_2$.

Like reference symbols and designations in the various drawings indicate like elements.

DETAILED DESCRIPTION

Fuel-driven bisegment Au—Pt nanowires exhibit autonomous self-propulsion due to electrocatalytic decomposition of hydrogen peroxide fuel. Such autonomous motion of catalytic nanowire motors can have various applications including drug-delivery, nanoscale assembly and transport, motion-based biosensing, etc.

Chemical Sensing Based on Catalytic Nanomotors: Motion-Based Detection of Trace Silver In one aspect, techniques, apparatus and systems are described for using catalytic nanomotors for motion-based chemical sensing, and particularly for specific detection of trace silver ions. Under electrochemically-triggered motion of catalytic nanowire motors, unusual speed acceleration is observed associated with silver ions generated at a pseudo silver-wire reference electrode placed in the vicinity of the nanowire motors. Such unexpected specific silver effect upon the speed of catalytic nanomotors can be used for designing a new motion-based silver sensing protocol. The new protocol relies on the use of an optical microscope for tracking the speed of nanowire motors and offers highly selective, sensitive and simple measurements of trace silver based on direct visualization.

Figure 1A:
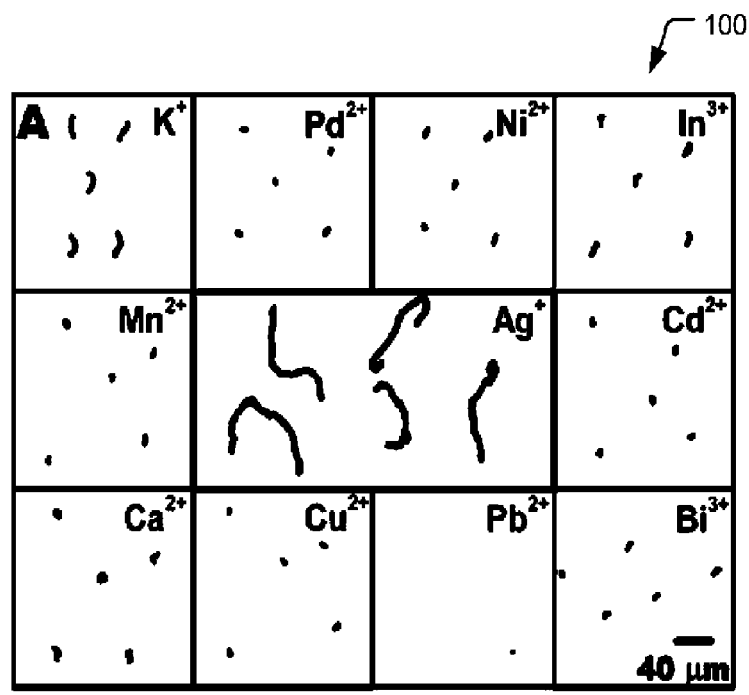
FIG. 1A is an image showing 3-sec movement of 5 randomly selected nanomotors in 11 motion of Au—Pt catalytic nanomotors in a 5% $H_2O_2$ solution containing 11 different 100 μM metal-nitrate salt solutions (of $K^+$, $Pd^{2+}$, $Ni^{2+}$, $Mn^{2+}$, $In^{3+}$, $Ag^+$, $Cd^{2+}$, $Ca^{2+}$, $Cu^{2+}$, $Pb^{2+}$ and $Bi^{3+}$).

FIG. 1A displays traces 100 of Au—Pt nanomotors (over a 3 second period), taken from videos of the nanowires in the presence of eleven different cations (100 μM each), along with the peroxide fuel. Ten of these cations caused a significant speed reduction, including a Brownian motion or a slower non-Brownian motion (with speeds ranging from 0.3 to 7.1 μm s$^{-1}$). Such slow speed (compared to an actual speed of ~10 μm s$^{-1}$ observed without these salts) is consistent with the self-electrophoresis mechanism for the propulsion of catalytic nanomotors, where the speed decreases linearly with the solution conductivity. In contrast, the nanomotors move over a dramatically longer path in the presence of silver (shown in the middle), displaying an average speed of 52 μm/s.

Figure 1B:
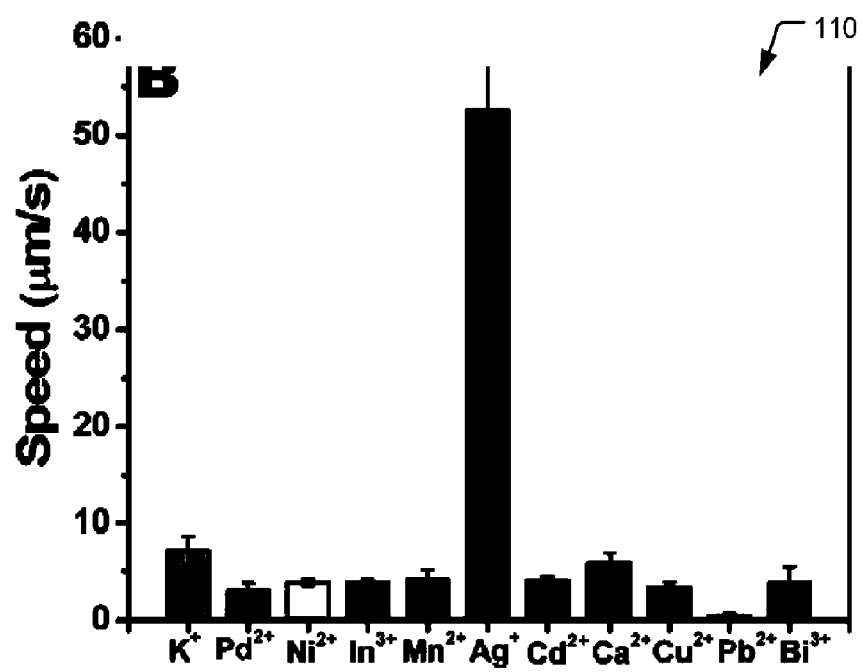
FIG. 1B is a corresponding bar graph comparing the average nanomotors speed of conditions in FIG. 1A.

Also shown in FIG. 1B is the histogram 110 depicting the average speed of the nanomotors in the presence of the different cations tested. These data clearly illustrate the remarkably selective acceleration in the presence of silver. Adding other cations (e.g., $Pb^{2+}$ or $K^+$ up to 5 μM) had only slight reductions in the speed signal in the presence of the silver analyte. The presence of a silver ion can greatly minimize the ionic-strength limitation of catalytic nanomotors. High speed of ~20 μm s$^{-1}$ was maintained in the presence of 0.1 mM $K^+$ (compared to a slow motion of 7 μm s$^{-1}$ observed for $K^+$ without the silver). Higher (>mM) salt concentrations, however, led to the expected conductivity-induced speed diminution.

Figures 2A, 2B, 2C, 2D:
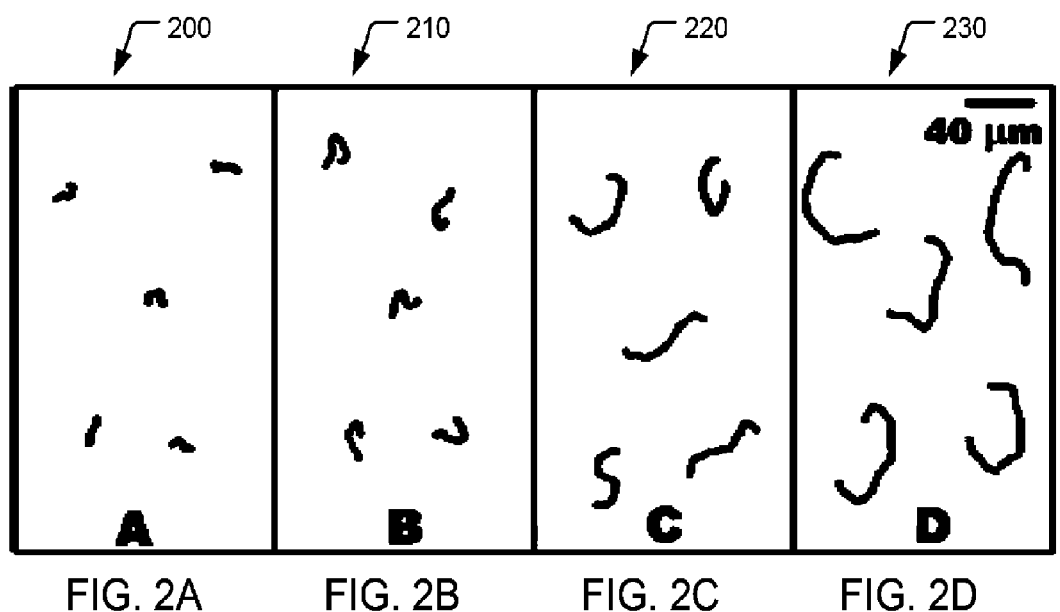
FIG. 2A shows track lines of nanomotors illustrating the distances traveled by five Au—Pt nanowires in the presence of 0 μM Ag concentration along with 5 wt % $H_2O_2$ fuel solution.
FIG. 2B shows track lines of nanomotors illustrating the distances traveled by five Au—Pt nanowires in the presence of 1 μM Ag concentration along with 5 wt % $H_2O_2$ fuel solution.
FIG. 2C shows track lines of nanomotors illustrating the distances traveled by five Au—Pt nanowires in the presence of 10 μM Ag concentration along with 5 wt % $H_2O_2$ fuel solution.
FIG. 2D shows track lines of nanomotors illustrating the distances traveled by five Au—Pt nanowires in the presence of 100 μM Ag concentration along with 5 wt % $H_2O_2$ fuel solution.
Figure 2E:
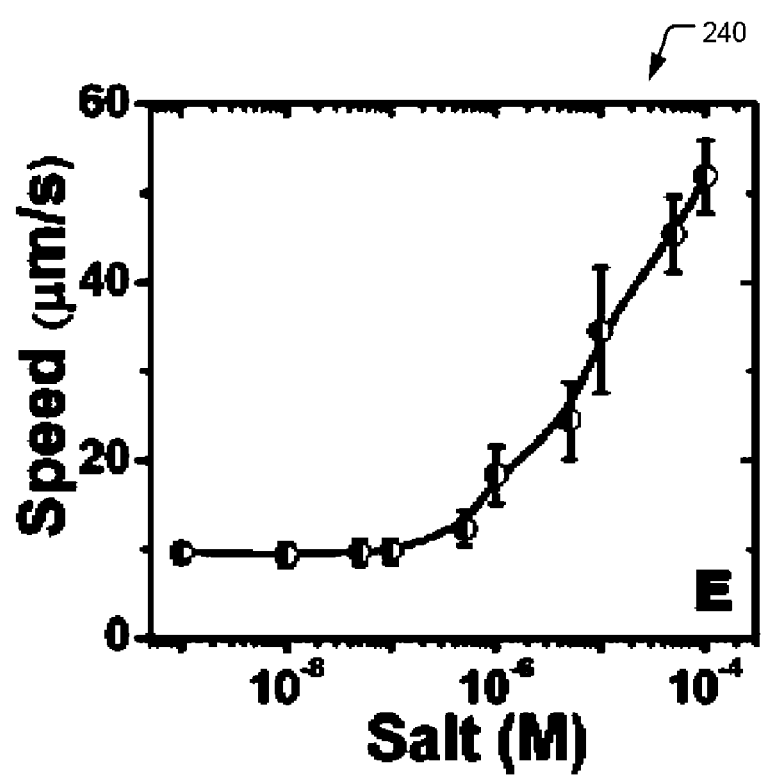
FIG. 2E is a calibration curve for Ag(I) over the micromolar range (0.5-100 μM with other conditions as in FIGS. 1A and 1B.

The highly selective motion-based response is characterized also with a defined concentration dependence, with the speed (or distance) providing the quantitative information. FIG. 2A, 2b, 2c and 2d displays track lines (200, 210, 220 and 230) of the catalytic nanomotors (over a 2 second period) obtained in the presence of different silver concentrations (0, 1, 10 and 100 μM). These traces indicate clearly that the nanomotors travel longer distances (ranging from 19-104 μm) upon increasing the silver concentration. Such paths correspond to speeds ranging from 9.6 μm s$^{-1}$ (without silver) to 52 μm s$^{-1}$ (at 100 μM silver). Also shown in FIG. 2E is a calibration plot 240 of the speed vs. silver concentration over the 10$^{-9}$ to 10$^{-4}$ M range. Such plot displays a defined concentration dependence over the 0.5 to 100 μM range, along with a negligible concentration effect at lower Ag(I) levels. The well-defined concentration dependence is clearly illustrated. The behavior observed in FIGS. 2A, 2B, 2C, 2D and 2E appear to be in conflict with what is commonly expected upon increasing the salt concentration.

Several possible mechanisms have been considered to explain the unusual acceleration of Au—Pt nanomotors in the presence of silver ions. One possible explanation relies on the underpotential deposition (UPD) of silver on the Au—Pt nanowires. With the addition of silver ions, these ions adsorb over the nanowire surface and are then reduced in the presence of hydrogen peroxide. Energy dispersive X-ray spectroscopy (EDX) measurements confirmed the presence of metallic silver over the Pt and Au segments of the nanowires (at 13 and 0.4 Ag atomic %, respectively), following a 0.5 hour exposure to the silver-nitrate/hydrogen-peroxide solution. A clear change of the color of the Pt segment was observed from analogous SEM experiments. No such compositional or color changes were observed in the presence of silver alone (without hydrogen peroxide). As will be illustrated below, a similar silver deposition was observed on platinum and gold nanorods. In addition, nanomotors exposed to a 100 μM Ag(I)/5% $H_2O_2$ solution for 0.5 and 24 hours, followed by an thorough wash with nanopure water, displayed high speeds of 20 and 35 μm s$^{-1}$, respectively, in a fresh silver-free 5% $H_2O_2$ solution. These data confirm that the deposited Ag(0), rather than the dissolved Ag(I), is responsible for the accelerated motion. The possibility of depositing Ag(0) by UPD onto gold nanorods and platinum surfaces was discussed by several groups.

Such silver deposition onto catalytic nanowires can lead to differences in the surface and catalytic properties (and hence to a faster the axial speed). Deposition of silver onto the Au segment increases the mixed potential difference (ΔE) between the anodic and cathodic segments, leading to an accelerated nanomotor motion in a manner similar to that reported recently for high-speed alloy nanomotors. Similarly, the silver deposition onto the Pt segment may make it a more catalytically active. The accelerated electrocatalytic decomposition of hydrogen peroxide was indicated also from the sharp decline of the motor speed following a 10 min exposure to the silver ion (compared to a longer ~30 min period observed without silver). The fast speed was then restored upon restoring the initial fuel level.

Figure 3:
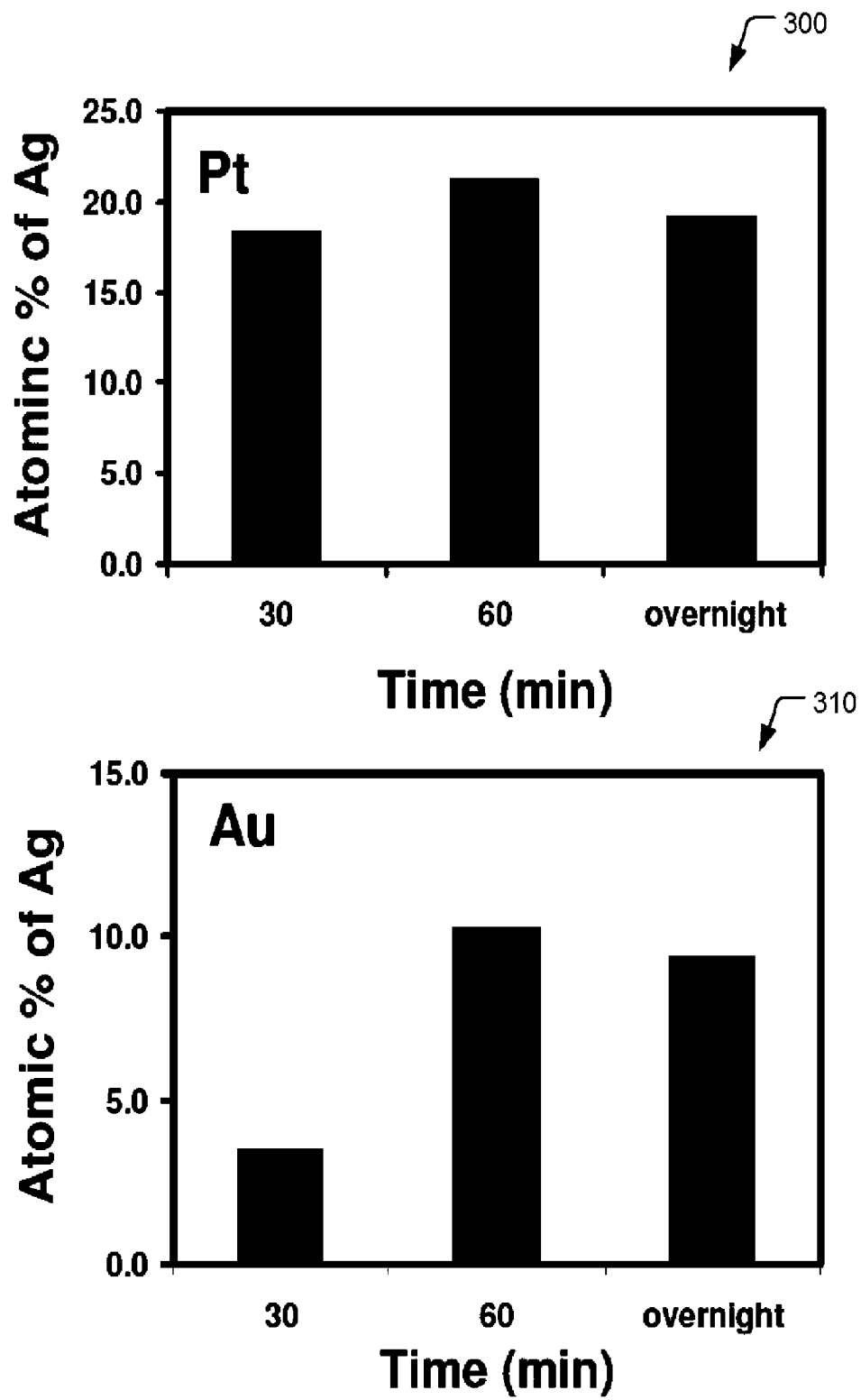
FIG. 3 are column graphs showing atomic % of Ag on monocomponent Pt and Au nanowires obtained from EDX measurements, where monocomponent Pt and Au nanowires were individually mixed with 5% $H_2O_2$ and 50 μM $AgNO_3$ and analyzed at different times.

To isolate the role of the individual segments upon the speed acceleration, the motility of monocomponent Pt and Au nanorods was examined in the presence of silver nitrate. Surprisingly, monocomponent Pt rods displayed a dramatic acceleration from 3.5 to 22.6 μm s$^{-1}$ in the presence of 10 μM silver ion. Monocomponent Au nanorods, in contrast, display a Brownian motion in the presence and absence of Ag(I). The EDX data (300, 310) of FIG. 3 confirm the presence of silver on monocomponent Pt and Au nanowires, with Ag(0) values of up to 18 and 10 (Ag atomic %), respectively. FIG. 3 shows atomic % of Ag on monocomponent Pt (300) and Au (310) nanowires obtained from EDX measurements. Monocomponent Pt and Au nanowires were individually mixed with 5% $H_2O_2$ and 50 μM $AgNO_3$ and analyzed at different times. The Ag(0) deposition onto monocomponent platinum nanowires leads to the asymmetry (bimetal character) essential to induce the electrocatalytic propulsion. This is in agreement with a recent hydrogen-peroxide based fuel cell study where a Pt—Ag (anode-cathode) combination exhibits the highest current density compared to other anode-cathode combinations, including Au—Ag one. Similarly, it was reported that Au—Ag bimetallic nanowire motors have a very slow speed of 6 μm s$^{-1}$. The self-diffusiophoresis mechanism may also be considered for explaining the silver effect. Here, the deposition of silver over the nanomotors increases the localized gradient of reaction products around the nanomotors, leading to a diffusiophoretic movement of nanomotor. Such ionic gradient around the nanomotors results in a net electric field in solution that facilitates the increased speed.

Motion-based chemical sensing involving fuel-driven nanomotors has been described. Effective measurements of trace Ag(I) have been accomplished based on the dramatic and specific acceleration of bimetal nanowire motors in the presence of this ion. These data clearly demonstrate the utility of catalytic nanomotors for measuring micromolar concentrations of silver. The presence of silver also facilitates the operation of catalytic nanomotors in conducting media that were not accessible earlier to catalytic nanomotors. While the described motion-based sensing has been illustrated for trace measurements of Ag(I), other sensing protocols are possible. For example, motion-based sensing can be applied in bioaffinity displacement assays based the ability of a target biomolecule to trigger the movement of an anchored nanomotor. Such motion-based bioassays can provide enhanced sensitivity, reflecting the ability to detect single-binding events.

Techniques, apparatus and systems are described for implementing autonomously propelling nanoscale machines for detecting motion transduction schemes, such as DNA hybridization in a fast, simple and highly sensitive manner. The motion-driven synthetic nanomotors for DNA sensing can measure changes in the speed of catalytic nanomotors induced by nanoparticle tags, such as those that include silver (Ag). The concentration-dependent distance signals can be visualized by optical microscopy, particularly via straight-line traces of magnetically-aligned 'racing' nanomotors, as illustrated for detecting low levels of $E.$ $coli$ bacteria. This nanomotor biodetection technique could be extended for monitoring a wide range of biomolecular interactions using different motion transduction schemes, thus providing a versatile tool for detecting biological targets.

Experimental Section

The gold/platinum nanomotors were prepared by sequential electrodeposition of gold and platinum into 200-nm-diameter nanopores of a 60 μm-thick alumina membrane template (Catalog No. 6809-6022; Whatman, Maidstone, U.K.). A thin gold film was first sputtered on the branched side of the membrane to serve as a working electrode. The membrane was assembled in a Teflon plating cell with aluminum foil serving as an electrical contact for the subsequent electrodeposition. A sacrificial copper layer was first electrodeposited into the branched area of the membrane using a 1 M cupric sulfate pentahydrate solution ($CuSO_4.5H_2O$; Sigma-Aldrich, St. Louis, Mo.), using a charge of 10 Coulombs and a potential of −1.0 V (vs. Ag/AgCl reference electrode) along with platinum wire as a counter electrode. Subsequently, Au segment was plated from a gold plating solution (Orotemp 24 RTU RACK; Technic Inc., Anaheim, Calif.) and electrodeposited at a total charge of 1.5 Coulombs and a potential of −0.9 V. Platinum was then deposited galvanostatically using a current of −2 mA for 50 min from a platinum plating solution (Platinum RTP; Technic Inc). The resulting Au—Pt nanowires had a length of around 2 μm. The sputtered gold layer and the copper sacrificial layer were simultaneously removed by mechanical polishing using cotton tip applicators soaked with 0.5 M $CuCl_2$ solution in 20% HCl. The nanomotors were then released by immersing the membrane in 3 M NaOH for 30 minutes. The synthesized nanomotors were separated from solution using by centrifugation at 10,000 rpm for 5 min and washed repeatedly with ultrapure water (18.2 MΩcm) until a neutral pH was achieved. Between the washing steps the nanomotors solution was mixed with ultrapure water and briefly sonicated (2-5 seconds) to ensure the complete dispersion of nanomotors in the washing water. All nanomotors were stored in ultrapure water at room temperature and their speed was tested before each experiment.

To prepare, 2 μm monocomponent nanowires, Pt was deposited for 70 min and Au was deposited for 2.5 C using the method described above. To study the deposition of Ag, bimetallic and monocomponent nanowires were individually mixed with 5% $H_2O_2$ and 50 μM $AgNO_3$ for different times. The residual silver ions and peroxide were removed by repeated washing with ultrapure water. Energy dispersive X-ray analyses (EDX) of the nanowires were performed using Phillips XL30 ESEM instrument to confirm the metal composition of nanowires.

To study the effect of silver ion (and of other cations) upon the motion of Au—Pt nanowire motors, the nitrate salts of the various metals were mixed with the nanomotor/fuel solution. Metal nitrate salts were purchased from Sigma or Fisher with a purity of 99.99% (or higher) to minimize potential impurity effects. The speed of the nanowire motors was examined in a solution prepared by mixing 50 μl of equal parts (1:1:1) of the diluted nanomotors suspension, the metal nitrate solution, and a freshly prepared 15 wt % $H_2O_2$ solution. A 10 μl aliquot of this solution was then added to the glass slide for immediate video acquisition.

The tracking of nanomotors was performed following the protocol reported earlier.1 An inverted optical microscope (Nikon Instrument Inc., Eclipse TE2000-S) equipped with a 20× objective, a Photometrics CoolSnap CF camera (Roper Scientific, Duluth, Ga.) and MetaMorph 7.1 software (Molecular Devices, Sunnyvale, Calif., USA) was used for capturing movies at a frame rate of 10 fps. This software calculates the instantaneous velocity by tracking the object's center-to-center displacement from frame to frame. The program averages the instantaneous velocities over the 50 frames tracked to yield an overall average speed. Usually 5 videos from randomly selected glass slide areas (200 μm×200 μm) were recorded to ensure accurate population sampling. Approximately, 20 random nanomotors were tracked for 50 frames to obtain a representative nanomotor speed. To distinguish between Brownian and non-Brownian motions, the motion of the nanomotors was compared to that observed without fuel. Typically, nanomotors in water display a Brownian motion, i.e. tumbling and/or sideways motion, with speeds of ~3 μm $s^{-1}$.

Motion-Based DNA Detection Using Catalytic Nanomotors

Chemically-powered nanomotors, particularly bisegment Au—Pt nanowires, exhibit autonomous propulsion due to the electrocatalytic decomposition of hydrogen peroxide fuel. An unusual increase can be detected in the speed of catalytic nanowire motors in the presence of silver ions. Such a dramatic silver-induced nanomotor speed enhancement can be utilized for detecting nucleic acid targets in a highly sensitive, rapid and simple hybridization assay through the use of silver nanoparticle tags.

In another aspect, described is a nanomotor-based biodetection platform for specific DNA and RNA detection. Silver-induced nanomotor speed enhancement is used in a sensitive, rapid and simple hybridization assay. The described motion-based hybridization sandwich assay can rely on the duplex formation of the nucleic acid target with a thiolated DNA capture probe and a silver nanoparticle tagged detector probe (SH-DP-Ag NPs). Subsequent dissolution of the Ag nanoparticle tags in the hydrogen peroxide fuel releases Ag ions, which, on adding an aliquot of the unmodified nanomotor solution, causes a substantial increase in their speed. The higher the concentration of the nucleic acid target, the more the silver nanoparticles (Ag NPs) that are captured, and the greater the nanomotor speed. The resulting distance signals can allow convenient measurements of the DNA target down to the attomole level. The described nanomotor concept may be readily expanded for detecting protein markers in connection with antibody or aptamer receptors. The motility of motor proteins can be applied for transporting and detecting target biomolecules. In this document, described are techniques, apparatus and systems for implementing synthetic nanomotors for transducing biorecognition events into motion. Such artificial nanomachines can address the limitations of using biological motors, including a limited lifetime in vitro and a narrow functioning range of environmental conditions.

Motion-Based Nucleic Acid Detection Assay

Figure 4A:
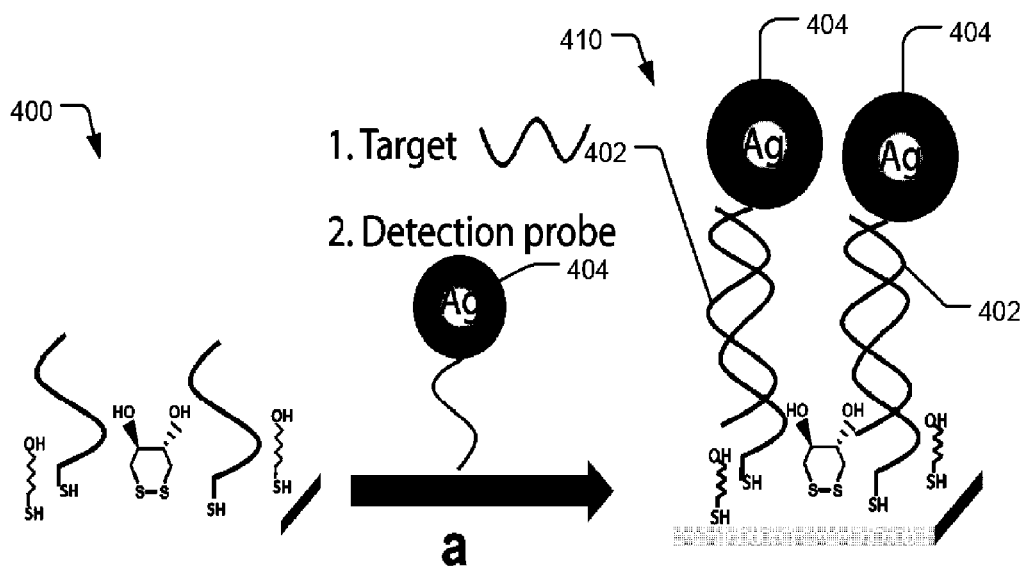
FIGS. 4A, 4B and 4C show motion based nucleic acid detection.
Figure 4B:
Figure 4C:
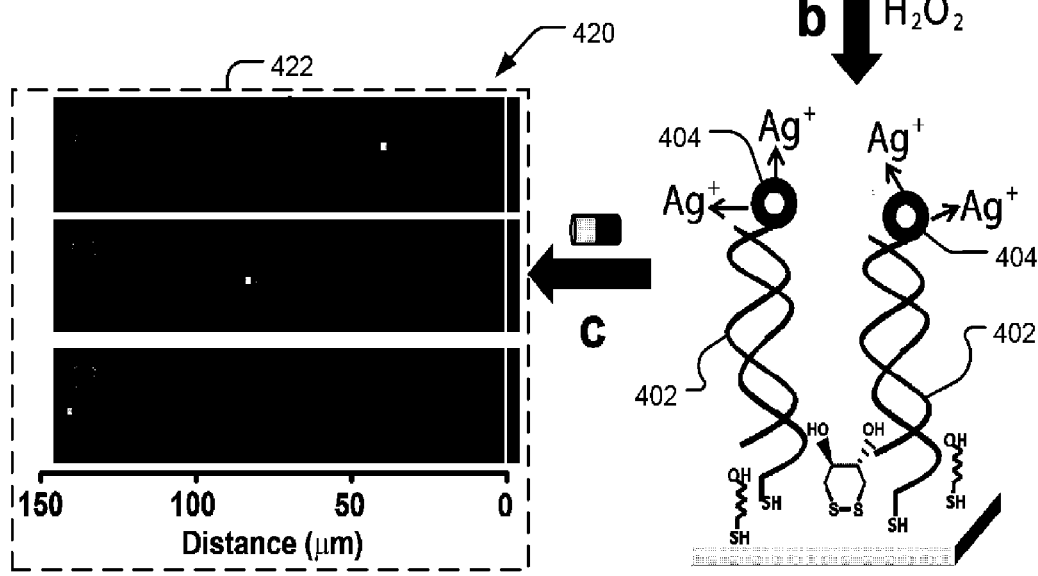

FIGS. 4A, 4B and 4C show an exemplary process for implementing motion based nucleic acid detection. FIG. 4A shows hybridization of the target and capture of the Ag nanoparticle-tagged detector probe in a typical sandwich assay on the ternary SH-CP/DTT+MCH surface, including washing of unbound SH-DP-Ag NPs (400). FIG. 4B shows dissolution of the silver nanoparticle tags in the peroxide fuel, leading to $Ag^+$-enriched fuel (410). FIG. 4C shows visual detection of the motion of the catalytic nanowire motors in the resulting $Ag^+$-enriched fuel (420). C1, C2 and C3 represent hypothetical and increasing target nucleic acid concentrations. Initially, a gold electrode is modified with a ternary monolayer composed of a thiolated capture probe (SH-CP), mercaptohexanol (MCH) and dithiothreitol (DTT). As illustrated in FIG. 4B, the presence of a complementary nucleic acid target (402) can lead to duplex formation with the nucleic acid target (402) and subsequent capture of the silver nanoparticle tags (SH-DP-Ag NP) (404). After a washing step to remove the excess unbound SH-DP-Ag NPs, hydrogen peroxide fuel is added, leading to rapid dissolution of the captured nanoparticle tags into silver ions ($Ag^+$) in the hydrogen peroxide fuel. This $Ag^+$-enriched fuel is separated from the surface of DNA modified gold electrode and directly added to an equal volume of freshly prepared nanomotor solution, thereby leading to a substantially increased nanomotor speed, and hence to concentration-dependent nanomotor distance signals. Such well-defined distance signals can be easily traced using optical microscopes, hence obviating the need for sophisticated analytical instruments. The higher the concentration of the DNA target, the more silver nanoparticles captured, and the greater the nanomotor speed. The resulting distance signal is thus proportional to the concentration of the DNA target 402 down to the attomole level, as indicated from the 'racing nanomotors' optical image 422 of FIG. 4C.

The described nanomotor sensing concept may be readily expanded for detecting protein markers in connection to antibody or aptamer receptors. Other approaches are possible for the motion transduction of molecular recognition events that could lead to a dramatically amplified signal readout mechanism for ultrasensitive biodetection. Such motion-based biosensing of molecular signatures represents a new paradigm in bioanalysis as it relies for the first time on the speed and distance (traveled by nanomotors) to add rich dimensions of analytical information. The described techniques use synthetic nanomotors for transducing biorecognition events into motion. Such artificial nanomachines address the limitations of using biological motors, including a limited lifetime in vitro and a narrow functioning range of environmental conditions.

Ag NP-Induced Nanomotor Acceleration

Silver nanoparticle tags, commonly used in optical or electrochemical DNA detection, are rapidly dissolved in the hydrogen peroxide fuel and the resulting silver ions lead to a dramatic speed increase of the nanomotors. The accelerated motion of catalytic nanomotors in the presence of silver nanoparticles (Ag NP) is illustrated in FIGS. 5a, 5b and 5c. FIG. 5A shows track lines 500 of nanomotors illustrating the distances traveled by three Au—Pt nanowires over a 1-second period in the presence of 10% $H_2O_2$ fuel (502, 504, and 506). FIG. 5B shows track lines 510 of nanomotors illustrating the distance traveled by three Au—Pt nanowires over a 1-second period in the presence of 10% $H_2O_2$ fuel containing 40 μM silver nanoparticles (512, 514 and 516). FIG. 5C shows two bar graphs 520 corresponding to FIGS. 5A (522) and 5B (524) comparing the traces of the three Au—Pt nanomotors in the presence of 10% $H_2O_2$ fuel without (FIG. 5A) and with (FIG. 5B) 40 pM silver nanoparticles. The nanowires exposed to the nanoparticles travel substantially longer distances compared to those present in the fuel solution without the nanoparticles (49.2 vs. 7.7 μm; FIG. 5C), thereby reflecting a 6.4-fold speed enhancement. FIG. 6 shows UV-Vis spectroscopy data that confirms the complete and instantaneous dissolution of Ag NPs in the peroxide fuel. The UV-Vis spectroscopy data includes spectra for 40 pM Ag nanoparticle water solution recorded before (600) and after (610) adding the 15% $H_2O_2$ solution. $Ag^+$ concentration of 40 μM was estimated from the number of ions released by a 40 pM silver-nanoparticle solution (based on the packing density ratio). The speed increase (to around 50 μm s$^{-1}$) observed for this $Ag^+$ concentration correlates well with the expected silver effect.

Motion Based Detection of DNA and E. coli 16S rRNA.

The instantaneous dissolution of metal nanoparticles in the fuel solution and the resulting silver-induced accelerated motion are the basis for using nanomotors to detect nucleic-acid hybridization. FIG. 7A shows traces 700 of three nanomotor movement over a 1 sec period in the presence of 15% $H_2O_2$ following complete hybridization assays using 0 nM target DNA (702, 704 and 706). FIG. 7B shows traces 710 of three nanomotor movement over a 1 sec period in the presence of 15% $H_2O_2$ following complete hybridization assays using 100 nM target DNA (712, 714 and 716). The differences in the movement of the three Au—Pt nanomotors swimming (over one sec period) in the peroxide fuel solution following complete hybridization assays with 0 and 100 nM DNA target can be seen by comparing FIGS. 7A and 7B. The corresponding column graph 720 is shown in FIG. 7C. Error bars represent n=20. The 100 nM DNA target leads to an average travel distance of 45.9 μm (724), compared to the 9.2 μm signal observed for the control hybridization experiment without target (722). Similar traces recorded for intermediate DNA target concentrations of 10 pM, 100 pM, 1 nM and 10 nM yielded increasing speeds of 11.5, 18.7, 24.9 and 31.5 μm s$^{-1}$, respectively. FIG. 8 is a calibration plot 800 for exemplary motion based DNA detection showing concentration dependence. The plot shows the nanomotor speed relationship with target DNA concentration in 15% $H_2O_2$. Error bars are for n=20 and * indicates a significance value of P<0.05.

Figures 9, 10:
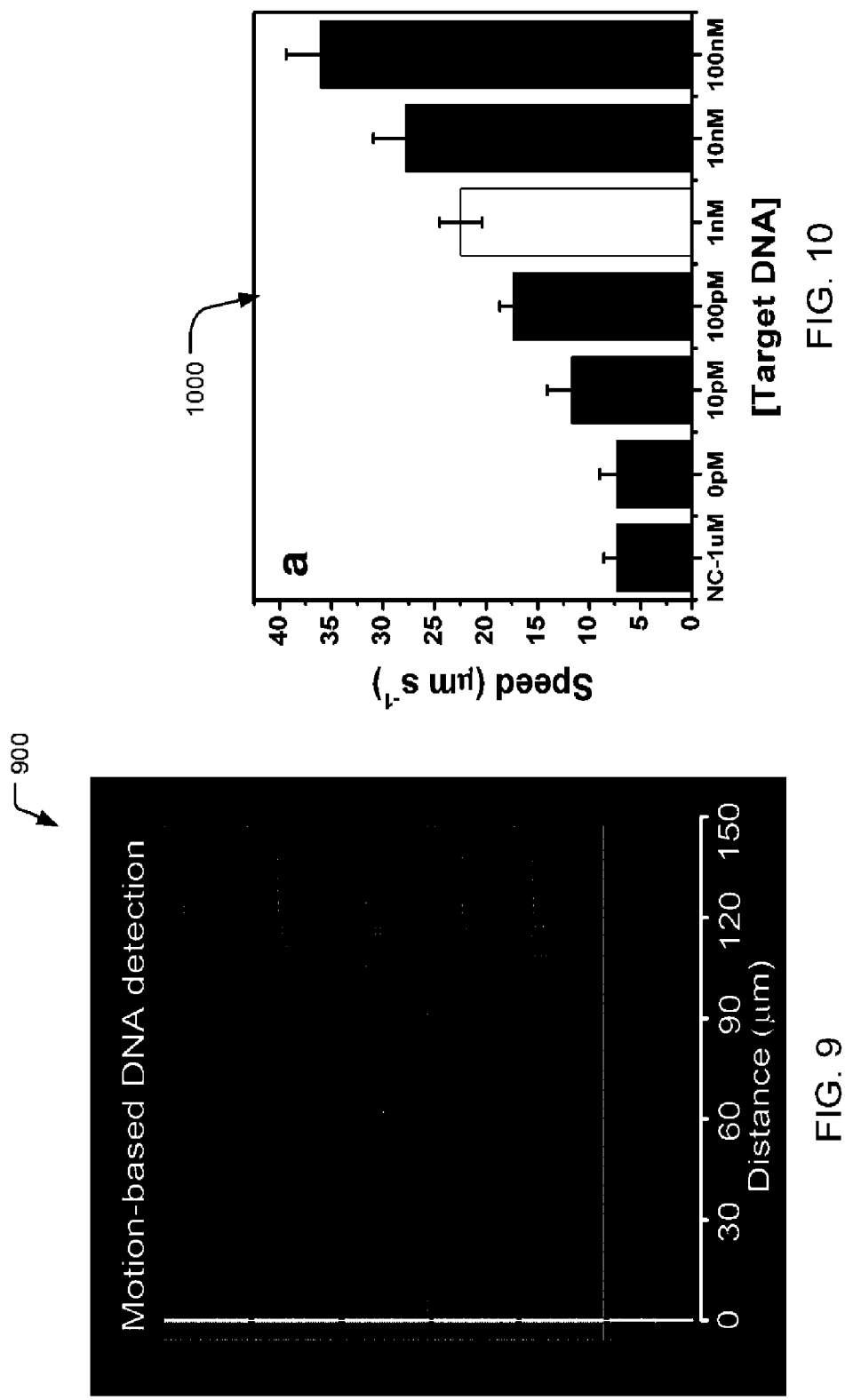
FIG. 9 shows nanomotor racing for quantitative nucleic acid detection.
FIG. 10 is a column graph 1000 showing the speed relationship with concentration of target DNA by the corresponding Au—Ni—Au—Pt nanomotors over a 4 sec period.

Straight-line distance signals of 'racing nanomotors', accomplished by incorporating a ferromagnetic nickel segment into the nanowire motors along with a directed magnetic alignment, provide an extremely convenient and attractive quantitation of the DNA targets. The optical images 900 of FIG. 9 illustrate such straight-line hybridization signals, recorded over a 4 sec period, for 4 μl samples containing increasing levels of the DNA target over the 40 amol –400 fmol range (i.e., 10 pM to 100 nM), along with the control (0 DNA) solution. Such directional motion control allows for clear visual comparison of the distance readouts of the different DNA concentrations. As expected, longer signals—ranging from 37.2 to 144.0 μm—are observed upon increasing the DNA concentration. FIG. 10 is a column graph 1000 showing the speed relationship with concentration of target DNA by the corresponding Au—Ni—Au—Pt nanomotors over a 4 sec period. Error bars are for n=20. A well-defined concentration dependence is therefore obtained over the broad 40 amol-0.4 pmol range as shown in FIG. 9 and FIG. 10.

In addition, straight-line 'race' of the Au—Ni—Au—Pt nanomotors in connection to the different DNA concentrations can be seen in FIG. 9 illustrating the attractive performance of the new motion biodetection platform. The nanomotor distance signal for the 40 amol DNA solution was shown to be statistically different when compared to a control, with an average speed of 9.3 µm s$^{-1}$ (vs. 7.3 µm s$^{-1}$, respectively). This detection limit compares favorably with those reported for other nanostructure-based DNA assays. Such value is particularly impressive considering the simplicity of the developed methodology and the absence of any deliberate amplification protocol, such as Ag enhancement or target PCR. Even lower levels of the DNA target could be detected by recording the distance signals over longer time, thereby making small concentration differences more discernable (in a manner reminiscent of increasing the electrophoresis-gel running time to distinguish between similarly sized fragments).

Figure 11:
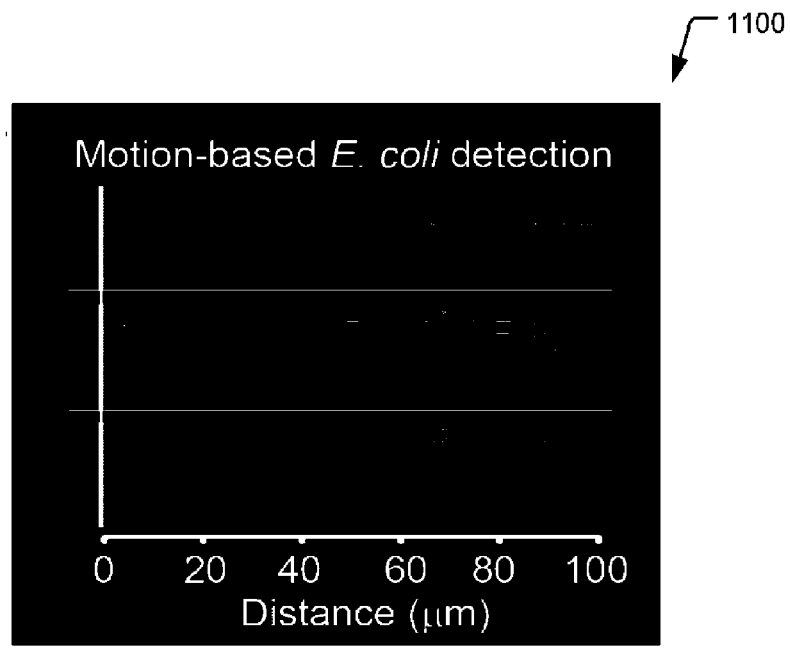
FIG. 11 shows nanomotor racing for quantitative *E. coli* 16S rRNA detection.
Figure 12:
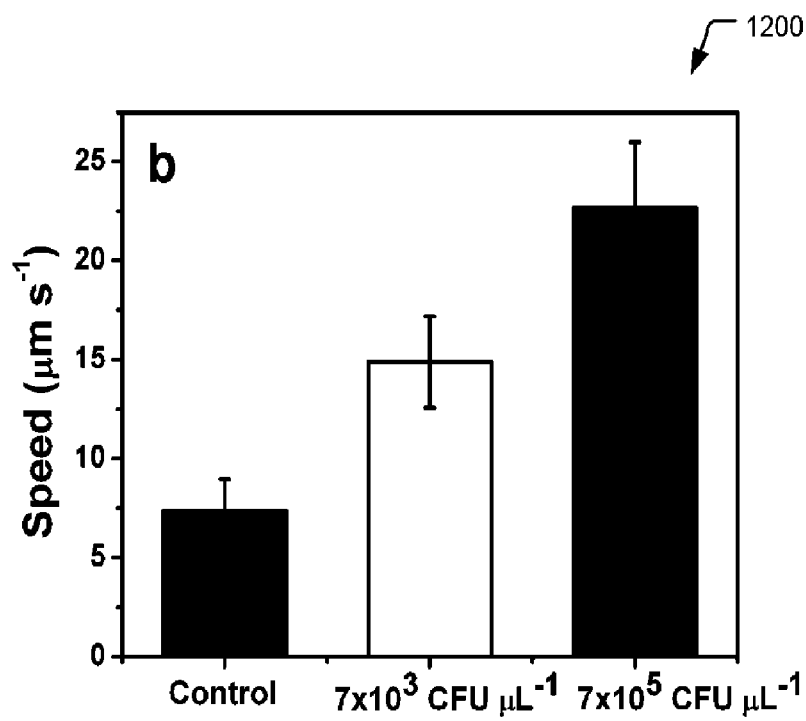
FIG. 12 is a column graph 1000 showing the speed relationship with *E. coli* 16S rRNA by the corresponding Au—Ni—Au—Pt nanomotors over a 4 sec period.

The practical utility of the described motion-driven DNA assay was illustrated using the same capture and detector probe for the detection of 16S rRNA released from E. coli pathogenic bacteria, obtained from a previously reported sample preparation. The optical images 1100 of FIG. 11 show catalytic nanomotors 'racing' following hybridization assays using different bacterial lysate solutions corresponding to different E. coli cells concentrations: 0, 7×10$^3$ and 7×10$^5$ CFU µl$^{-1}$ leading to average distance signals of 32, 56 and 96 µm, respectively. FIG. 12 is a column graph 1200 showing the speed relationship with concentration of pathogenic E. coli 16S rRNA by the corresponding Au—Ni—Au—Pt nanomotors over a 4 sec period. Error bars are for n=20. The results indicate a sensitive detection of the genetic material corresponding to around 2,000 E. coli CFU µl$^{-1}$ level.

Specificity and Precision Studies.

Figure 13A:
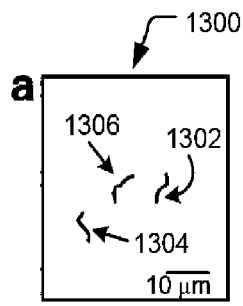
FIGS. 13A, 13B, 13C, 13D, 13E, 13F, 13G, 13H and 13I show specificity of the motion-driven DNA detection.
Figure 13B:
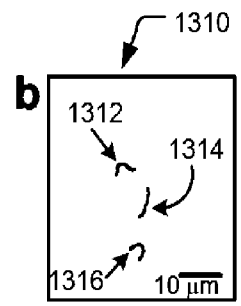
Figure 13C:
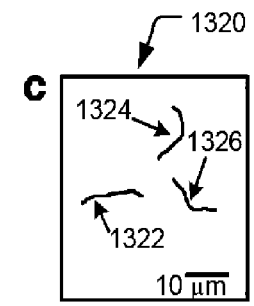
Figure 13D:
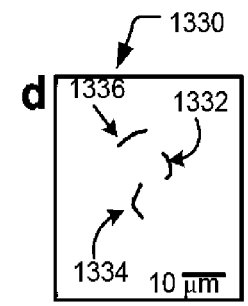
Figure 13E:
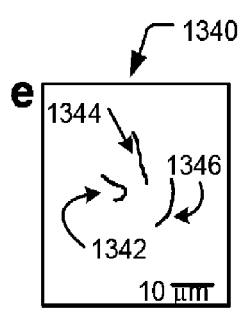
Figure 13F:
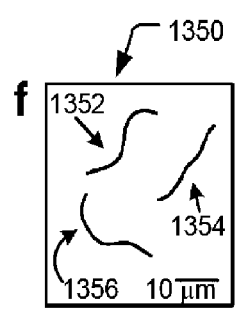
Figure 13G:
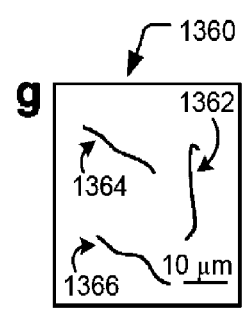
Figure 13H:
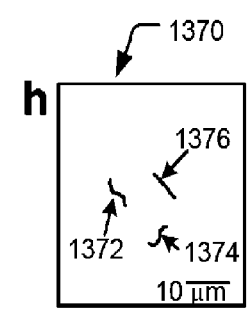
Figure 13I:
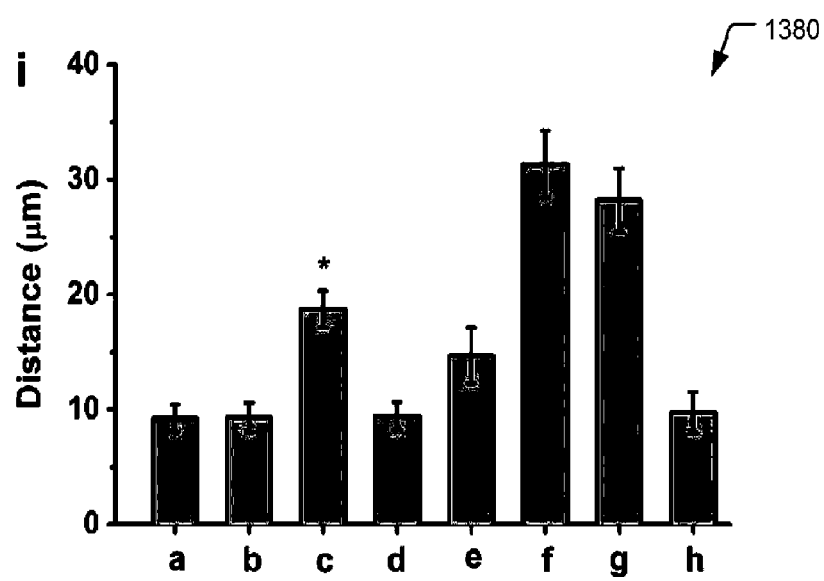

The specificity of the motion sensing protocol was examined by challenging the system with excess of various non-complementary and mismatched oligonucleotides. FIGS. 13A, 13B, 13C, 13D, 13E, 13F, 13G, 13H and 13I show specificity of the motion-driven DNA detection. FIG. 13A shows track lines 1300 illustrating the distances traveled by three nanomotors over a 1 sec period in 15% H$_2$O$_2$ after hybridization with 0 nM target DNA (normal control) (1002, 1004 and 1006). FIG. 13B shows track lines 1310 illustrating the distances traveled by three nanomotors over a 1 sec period in 15% H$_2$O$_2$ after hybridization with large excess (1 µm) of a non-complementary DNA (1312, 1314 and 1316). FIG. 13C shows track lines 1320 illustrating the distances traveled by three nanomotors over a 1 sec period in 15% H$_2$O$_2$ after hybridization with 100 pM of the target DNA (1322, 1324 and 1326). FIG. 13D shows track lines 1330 illustrating the distances traveled by three nanomotors over a 1 sec period in 15% H$_2$O$_2$ after hybridization with large excess (1 µm) of a three-base mismatched oligonucleotide (1332, 1334 and 1336). FIG. 13E shows track lines 1340 illustrating the distances traveled by three nanomotors over a 1 sec period in 15% H$_2$O$_2$ after hybridization with 10 nm of a two-base mismatched oligonucleotide (1342, 1344 and 1346). FIG. 13F shows track lines 1350 illustrating the distances traveled by three nanomotors over a 1 sec period in 15% H$_2$O$_2$ after hybridization with 10 nM of the target DNA (1352, 1354 and 1356). FIG. 13G shows track lines 1360 illustrating the distances traveled by three nanomotors over a 1 sec period in 15% H$_2$O$_2$ after hybridization with 16S rRNA corresponding to 5×10$^5$ CFUµl$^{-1}$ E. coli (1062, 1064 and 1066). FIG. 13H shows track lines 1370 illustrating the distances traveled by three nanomotors over a 1 sec period in 15% H$_2$O$_2$ after hybridization with 16S rRNA corresponding to 7×10$^5$ CFUµl$^{-1}$ K. pneumoniae (1372, 1374 and 1376). The scale bar represents 10 µm. The corresponding column graph 1380 in FIG. 13I provides a quantitative summary of these data. As expected, the system responds favorably to the target DNA with well defined distance signals of 18.7 and 31.5 µm for the 100 pM and 10 nM levels, respectively. In contrast, huge excess (1 µM) of non-complementary (FIGS. 13b) and 3-base mismatched (FIG. 13d) oligonucleotides displays a negligible change in the response (compared to the control signal without the nucleic acid; FIG. 13a). Only the 2-base mismatched DNA yields a defined signal of 14.7 µm (compared to 31.5 µm for a similar level of the complementary DNA target, FIG. 13f). Such response reflects the partial duplex formation of the mismatch, hence the capture of the silver nanoparticle 'accelerating' tags. Overall, the data of FIGS. 13A, 13B, 13C, 13D, 13E, 13F, 13G, 13H and 13I indicate that the motion detection platform offers high specificity, reflecting the negligible non-specific adsorption of the Ag-tagged detector probe onto the mixed self-assembled monolayer on the gold surface. The small background contributions compare favorably with those of analogous nanoparticle-based bioassays. Further discrimination against more closely mismatched oligonucleotides, such as single mismatched DNAs, could be achieved by using stringent control of the hybridization conditions or highly specific PNA capture probes.

The specificity of the motion-driven bioassay was also tested using a biological control. Klebsiella pneumoniae (K. pneumoniae), another gram-negative pathogenic Enterobacteriaceae. As illustrated in FIGS. 13G and 13H, and contrary to the signal of E. coil 16S rRNA (average speed of 28.2 µm s$^{-1}$, FIG. 13G), the nanomotor response to the presence K. pneumoniae 16S rRNA (average speed of 9.7 µm s$^{-1}$, FIG. 13H) is similar to that observed for the negative control (without target, average speed of 9.2 µm s$^{-1}$, FIG. 13A). This demonstrates the high specificity of the motion bioassay towards the E. coli 16S rRNA target (versus other non-complementary bacterial RNAs) and the absence of non-specific adsorption of the SH-DP-Ag NPs. These results demonstrate the high specificity of the selected capture probe for binding only 16S rRNA in E. coli lysates despite the potential conservation of the 16S rRNA gene.

Figures 14A, 14B:
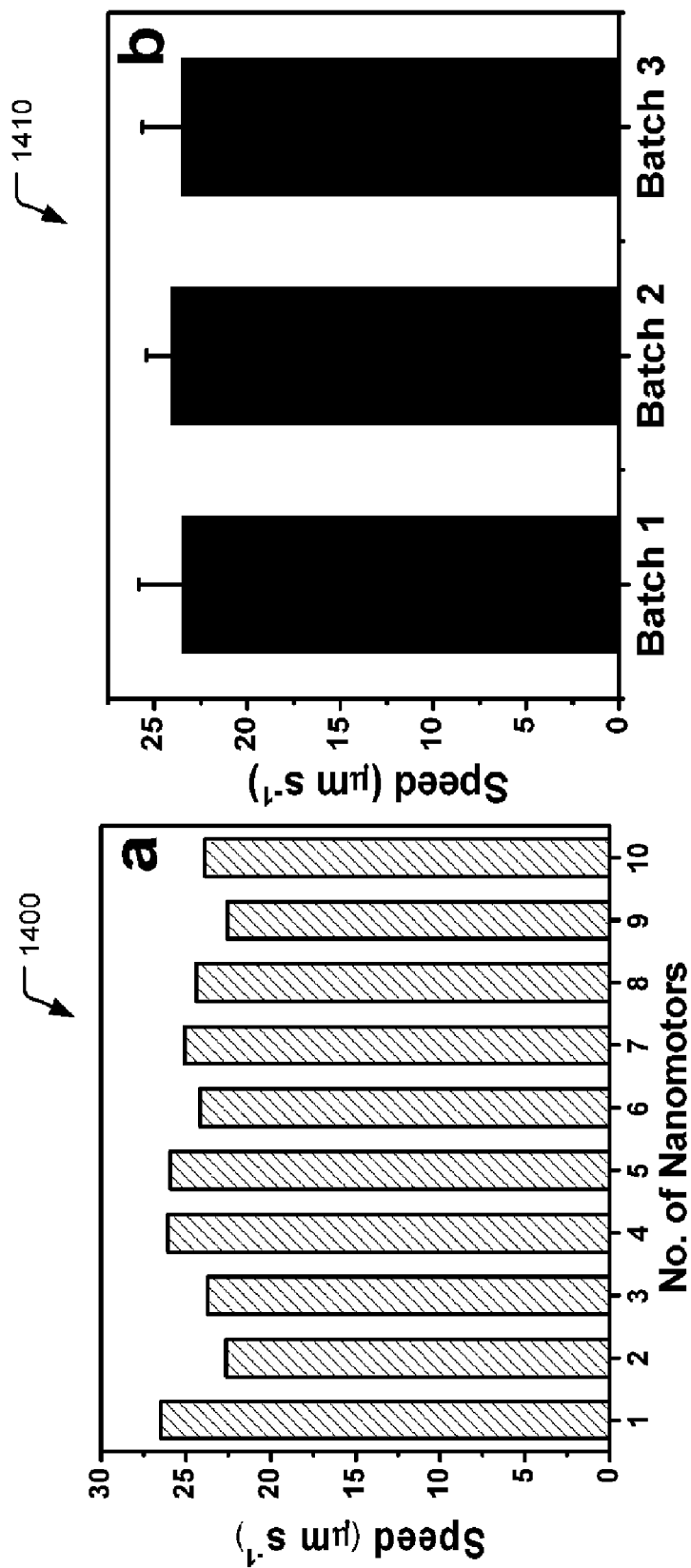
FIGS. 14A and 14B show precision of motion based DNA detection.

The precision of the described motion-driven biodetection platform was also examined. FIG. 14A displays speed signals (1400) of 10 different nanomotors for a 1 nM DNA target solution. Well-defined and reproducible speed signals are observed, leading to a favorable relative standard deviation (RSD) of 5.66%. Similarly, nanomotor speed variability between 3 different experimental batches (1410) revealed negligible differences (P<0.05) in connection to 1 nM DNA target, as shown in Supplementary FIG. 14B.

Described in this document are techniques, apparatus and systems for implementing synthetic nanomotors as bioanalytical tool in connection to the detection of DNA and bacterial rRNA. Such motion-based DNA sensing relies on the use of an optical microscope for directly tracking changes in the speed of unmodified nanowire motors. The silver ion-induced nanomotor acceleration reflects the sandwich formation between the capture probe, complementary target and the Ag nanoparticle tagged detector probe. The nanoparticle-induced nanomotor acceleration reflects the dramatically enhanced speed of catalytic nanomotors in the presence of silver ion. The resulting motion driven biodetection strategy offers sensitive and selective, easily measured distance readouts down to the 40 amol DNA level and the ability to detect directly raw bacterial ribosomal RNA without isolation or purification steps. Unlike common nanoparticle-based silver enhancement DNA optical or electrochemical hybridization assays, the nanomotor method requires no such particle enlargement (and hence is not susceptible to non-specific Ag precipitation) and relies on portable, simple and low-cost instrumentation. Motion-based biosensing can be expanded to multiplexed measurements of multiple targets by encoding functionalized nanomotors with a multistripe barcode segment. The template nanowire preparation route allows adding a multistripe Ag—Au section to the Pt—Au nanomotor, hence facilitating rapid reflectivity identification. An internal standard could also be used in the new motion detection to facilitate the quantitation of the nucleic acid target and address rare potential variations between nanomotor batches. Also, the new nanomotor speed transduction can facilitate the collection of multiple readings in a single experiment, thereby contributing to the overall reliability of the proposed protocol. The sensitivity and selectivity could be even further enhanced by recording the distance signals over longer periods of time and by using specific PNA probes, respectively. Since the sensitivity of real-life nucleic acid measurements is commonly limited by non-specific adsorption signals we used here a new multi-component ternary monolayer that effectively minimizes such non-specific background contributions compared to commonly used binary monolayers. A huge excess of non-complementary DNA or rRNA from a different bacteria thus has a negligible effect upon the fully complementary target (DNA or rRNA) distance signals.

Motion driven biosensing represents a new paradigm in bioanalysis as it relies for the first time on the speed and distance as the analytical signal. While the concept has been presented in connection to motion based DNA biodetection and silver nanoparticle tags, it may be extended to the detection of a broad range of target biomolecules in connection to different biomolecular interactions and motion transduction principles. Such new approaches to transduce the biomolecular recognition event into nanomotor motion are currently being examined in our laboratory. The distance signals can be translated into analytical results using low cost microscopic readers thereby making the new method affordable and attractive for low resource settings. Owing to its attractive features we expect that the new motion based signal transduction will lead to a host of novel and powerful biosensing applications, including clinical diagnostics, biothreat detection, food safety and forensic analysis.

Reagents

Silver nanoparticles (Ag NPs) (diam. 20±5 nm given by the manufacturer) were purchased from Ted Pella Inc (Cat No. 15705-20SC). 6-Mercapto-1-hexanol (MCH), sodium dodecyl sulfate (SDS), dithiothreitol (DTT), trizma hydrochloride (Tris-HCl), ethylenediaminetetraacetic acid and bovine serum albumin were obtained from Sigma-Aldrich and used without further purification. The blocking agent casein was obtained from Pierce.

The buffer solutions used were as follows: The DNA immobilization buffer (IB) was 10 mM Tris-HCl, 1 mM ethylenediaminetetraacetic acid, and 0.3 M NaCl (pH 8.0). The hybridization buffer (HB) was a 1M phosphate buffer solution containing 2.5% bovine serum albumin and 0.05% casein (pH 7.2). The storage buffer (SB) for SH-DP-Ag NPs contained 10 mM phosphate buffer, 300 mM NaCl and 0.01% SDS (pH 7.2).

The sequences of the oligomers used for the detection of synthetic 30-mer oligonucleotide or *E. coli* 16S rRNA targets are given in the Supplementary Table. All thiolated oligonucleotides were purchased from Integrated DNA Technologies. Other oligonucleotides, i.e., the complementary and non-complementary targets, were obtained from Thermo Fisher Scientific. According to the sandwich protocol the SH-CP was immobilized on the gold surface while the SH-DP was conjugated with Ag nanoparticle tags.

Bacterial strains of *E. coli* (NEB 5-α) and *Klebsiella pneumoniae* (KP210) were obtained from the University of California-Los Angeles. The isolates were stored at −80° C. and were freshly lysed before each experiment.

Preparation of Nanomotors.

The Au—Pt nanomotors were prepared by sequential electrodeposition of gold and platinum into 200-nm-diameter nanopores of a 60 μm-thick alumina membrane template (Catalog No. 6809-6022; Whatman)[13]. Briefly, the branched side of the membrane was sputtered with a thin gold film, followed by electrodeposition of a sacrificial copper layer from a 1 M cupric sulfate pentahydrate solution ($CuSO_4.5H_2O$; Sigma-Aldrich), using a charge of 10 Coulombs and a potential of −1.0 V (vs. Ag/AgCl reference electrode) along with a platinum wire counter electrode. Subsequently, Au segment was plated from a gold plating solution (Orotemp 24 RTU RACK; Technic Inc.) and electrodeposited at a total charge of 1.5 Coulombs and a potential of −0.9 V. Platinum was then deposited galvanostatically using a current of −2 mA for 50 min from a platinum plating solution (Platinum RTP; Technic Inc). Similarly, magnetic Au—Ni—Au—Pt nanomotors were prepared by introducing a ferromagnetic Ni segment. Following an initial segment of 0.75 C gold, 2 C of Ni was electrodeposited at −1.0 V (vs. Ag/AgCl) from a plating solution [20 g $l^{-1}$ $NiCl_2.6H_2O$, 515 g $l^{-1}$ $Ni(H_2NSO_3)_2.4H_2O$ and 20 g $l^{-1}$ $H_3BO_3$ (buffered to pH 3.4)]. Subsequently, the second gold segment (0.75 C) and a platinum segment were electrodeposited as above. The sputtered gold layer and the copper sacrificial layer were sequentially removed by mechanical polishing using cotton tip applicators soaked with 0.5 M $CuCl_2$ solution in 20% HCl. The nanomotors were then released by immersing the membrane in 3 M NaOH for 30 minutes. The synthesized nanomotors were separated from solution using by centrifugation at 2,300 g for 5 min and washed repeatedly with ultrapure water (18.2 MΩ·cm) until a neutral pH was achieved. Between the washing steps the nanomotors suspension was mixed with ultrapure water and briefly sonicated to ensure the complete dispersion of nanomotors. All nanomotors were stored in ultrapure water at room temperature and their speed was tested before each experiment to identify potential nanomotor 'malfunction'.

Conjugation of SH-DP with Ag NPs.

SH-DP-Ag NPs was prepared in accordance to earlier studies[24-27]. The silver colloid (0.12 nM given by the manufacturer) was concentrated 10 times by centrifugation (16,770 g, 15 min) and redispersed in nanopure water to give final concentration of 1.2 nM. Appropriate aliquots of SH-DP were added (final conc. 10 μM) to 100 μl of this 1.2 nM Ag NPs solution before incubating for 2 hours. SDS solution (1%) and 100 mM pH 7.2 phosphate buffer solution were added to the above mixture to reach final solution concentrations of 0.01% and 10 mM, respectively. The solution was kept for gentle shaking overnight. Small aliquots of 2 M NaCl were added over 48 hours to raise the final NaCl concentration to 500 mM, followed by another overnight incubation. Subsequently, the excess of SH-DP was removed by centrifugation (24,150 g, 10 min) and redispersed in the SB, a procedure repeated three times.

Assembling the Capture Probe at the Gold Surface.

DNA hybridization was performed on an array of 16 gold electrodes (each 2.5 mm diam.; GeneFluidics Inc.). Initially, 10 µM freshly prepared DTT was added to SH-CP (0.5 µM) in IB and allowed to stand for 10 min. A 6 µL aliquot of this SH-CP solution was drop cast to cover each Au sensor and stored overnight in a 4° C. in a humidified surrounding. After washing with ultrapure water, the probe-modified Au sensors were treated with 6 µl of the 1 mM MCH aqueous solution for 50 min to obtain a ternary self-assembled monolayer. Finally, the sensors were thoroughly rinsed with ultrapure water and dried under nitrogen.

DNA Hybridization Assay.

The DNA detection strategy is illustrated in FIGS. 1A, 1B and 1C. Different concentrations of the DNA target (or non-complementary and mismatched oligos) were prepared in the HB. Aliquots (4 µl) of this target solution were cast on each of SH-CP modified gold sensors and were incubated for 15 min. After the sensors slightly rinsed by ultrapure water and dried by $N_2$, a 4 µl of SH-DP-Ag NPs conjugation solution was cast on each sensor and was incubated for 30 min. After incubation, each sensor was thoroughly rinsed and subsequently washed with ultrapure water in a shaker (300 rpm) for 5 min and dried with $N_2$. These sensors were immediately used for the nanomotor based hybridization assay.

Bacterial 16S rRNA Hybridization Assay.

The bacterial 16S rRNA target, derived from single-step bacterial lysis, was detected using the same thiolated capture probe and Ag NPs-modified detector probe, in a manner similar to the synthetic 30-mer target DNA detection. The bacteria were initially lysed by resuspension of the appropriate pellet containing ~$10^7$ CFU bacteria in 10 µl of 1 M NaOH and incubation for 5 min. A 50 µl aliquot of HB was added to this 10 µl bacterial lysate, leading to genetic material corresponding to ~$10^7$ CFU per 60 µl (final pH 7.8). This solution was serially diluted in HB to provide different concentrations of bacterial genetic material (16S rRNA). Aliquots (4 µl) of this raw bacterial target were cast on each capture-probe modified sensor for 15 min, followed by hybridization with SH-DP-Ag NPs, and washing, dissolution and detection steps. All procedures were carried out at room temperature.

Nanomotor Motion Based Readout for Hybridization Detection.

Silver-ion induced motion based sensing protocol described earlier was used for detecting the DNA and E. coli 16S rRNA. For this purpose, 5 µl of $H_2O_2$ (30%) was dropped on the sensor modified with the sandwich hybridized duplexes for 2 min to dissolve Ag NPs to $Ag^+$. The assay was completed by mixing the above $Ag^+$-enriched $H_2O_2$ fuel solution with equal volume of freshly prepared nanomotors in ultrapure water. The resulting mixed solution was then added to the glass slide for immediate video acquisition and tracking. The tracking of nanomotors was performed following the protocol reported earlier. An inverted optical microscope (Nikon Instrument Inc., Eclipse TE2000-S) equipped with a 40x objective, a Photometrics CoolSnap CF camera (Roper Scientific) and MetaMorph 7.1.7 software (Molecular Devices) was used for capturing movies at a frame rate of 10 fps. This software calculates the instantaneous velocity by tracking the object's center-to-center displacement from frame to frame. Usually 5 videos from randomly selected glass slide areas (200 µm×200 µm) were recorded to ensure accurate population sampling. Approximately, 20 random nanomotors were tracked for 50 frames to obtain a representative nanomotor speed. Bonferroni-corrected Anovas ($P<0.05$) and power calculations were performed on all the data sets to determine the detection limit and identify statistically significant concentrations.

Nanomotor Design

Figure 15A:
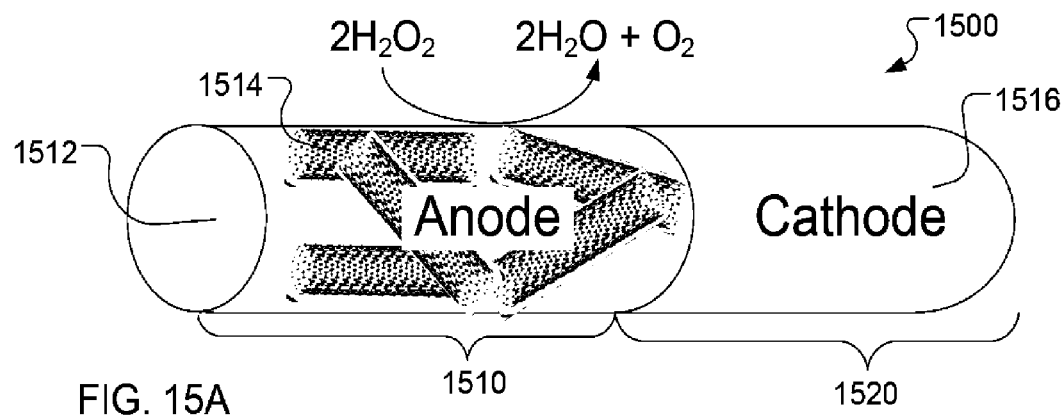
FIGS. 15A, 15B and 15C are block diagrams showing exemplary bimetal nanomachine.
Figure 15B:
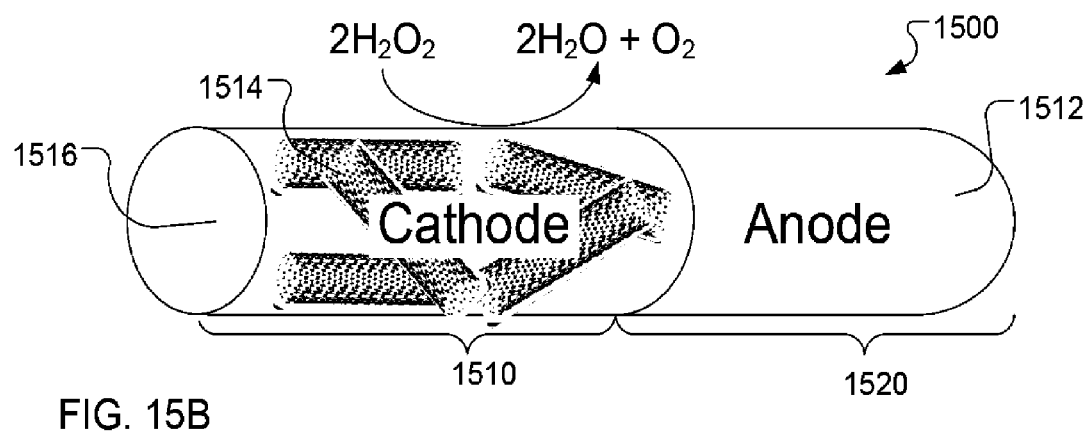
Figure 15C:
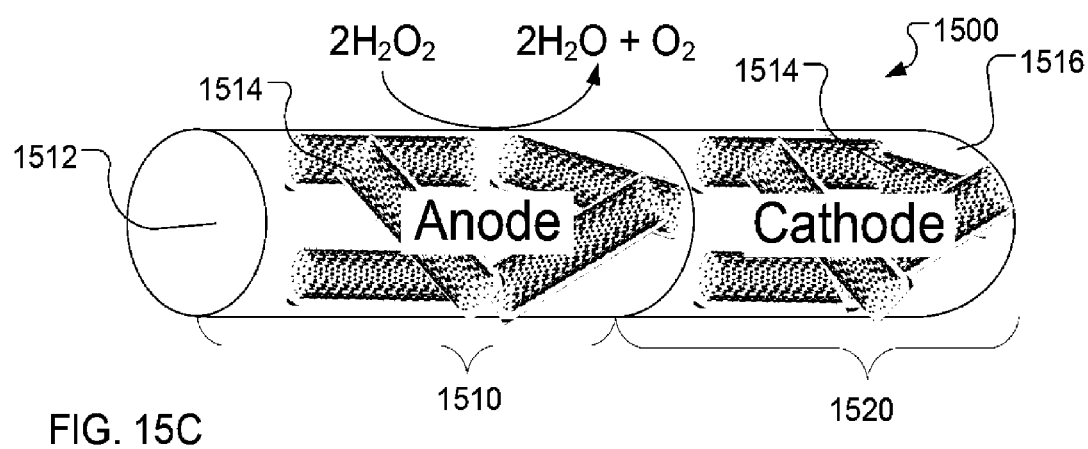

FIGS. 15A, 15B and 15C are block diagrams showing exemplary bimetal nanomachine 100. The nanomachine 1500 can be implemented as a bimetal nanowire that includes an anode component 1510 connected to a cathode component 1520. The anode component 1510 can include one or more oxidizing catalysts 1512, such as platinum (Pt), silver (Ag), palladium (Pd), nickel (Ni) other transition metal or a combination of them. For example, Pt, Ag and Pd are known catalysts for peroxide decomposition.

In addition, one or more non-metallic catalysts 1514 can be incorporated into the anode component 1510. The non-metallic catalysts 1514 include graphite or carbon-based catalysts such as carbon-nanotubes (CNTs), a fullerene ($C_{60}$) structures or graphite structures with edge-plane-like defects. Carbon and graphite, in various forms, can be an attractive electrode material. The surface structure of carbon-based can affect the electrochemical and chemical reactivity of electrodes based on these materials. In particular, the catalytic activity, electron transfer and chemical reactivity of graphitic carbon electrodes may be attributable to the surface defect sites, and in particular edge-plane-like defect sites. Fullerenes are a family of carbon allotropes, molecules composed entirely of carbon, in the form of a hollow sphere, ellipsoid, tube, or plane. The non-metallic catalyst can be incorporated within the anode component 1510 by combining CNTs with Pt 1512, for example. The non-metallic catalyst 1514 should be incorporated into the anode component 1510 to expose at least a portion of the non-metallic catalysts to an environment external to the surface of the anode component 1510. In some implementations, the non-metallic catalyst can be incorporated on the external surface of the anode component 1510. Further, the non-metallic catalyst can be incorporated both within the anode component 1510 and on the external surface of the anode component 1510. The cathode component 1 520 can include one or more reduction catalyst or electron acceptor 1516, such as gold (Au) that catalytically reduces peroxide and oxygen. In some implementations, the non-metallic catalyst 1514 can be incorporated into the cathode component 1520. For example, CNTs can be combined with Au in the cathode component 1520. As described above, the CNTs incorporated into the cathode must be at least partially exposed to the environment external to the cathode component 1520. Alternatively, the non-metallic catalyst can be applied on the external surface of the cathode component. Further, the non-metallic catalyst 1514 can be incorporated both within the cathode component 1520 and on the external surface of the cathode component 1520. In some implementation, the non-metallic catalyst can be incorporated within (and/or on external surface) of both the anode 1510 and cathode components 1520.

The CNTs 1514 can be implemented as purified multi-walled carbon-nanotubes (from NanoLab of Newton, Mass., for example). In brief, CNTs are dispersed in a concentration of nitric acid and sonicated. For example, 100 milligram (mg) of CNTs can be dispersed in 100 milliliter (ml) of concentrated nitric acid and sonicated at 60° C. for 90 min. The CNT-nitric acid solution is then incubated at a select temperature for a select period of time. For example, the CNT-nitric acid solution can be incubated at 60° C. overnight. Following the acid treatment and sonication, the CNT suspension is centrifuged (at 3000 rpm for 30 min, for example) to separate the CNTs from the acid solution. The acid treated CNTs are washed repeatedly with nanopure water (18.2 MΩ, for example) until the solution pH reaches near neutral state. The purified CNTs are dried (at 60° C., for example) until a constant mass is obtained. All CNT containing solutions are sonicated (for 2 hours, for example) prior to use.

The bi-segment or bimetal nanomotors 1500 can be prepared by electrodepositing the corresponding metals or hybrid metal-CNT into a porous alumina membrane template (from Whatman of Maidstone, U.K.). The length (~1 µm) of each nanomotor component (anode and cathode) can be selected by controlling the electrodeposition charge. The diameter (~220 nm) of each nanomotor component was predetermined by the pore size of the membrane.

To generate the cathode component 1520, a thin gold film is first sputtered on the branched side of the membrane to serve as a working electrode. The membrane is assembled in a plating cell with aluminum foil serving as an electrical contact for the subsequent electrodeposition. In order to synthesize well-shaped cylindrical nanomotors, a sacrificial silver layer is electrodeposited into the branched area (~1-2 µm thickness) of the membrane using a silver plating solution (1025 RTU@4.5 Troy/Gallon; Technic Inc., Anaheim, Calif.) and a total charge of 2 coulombs (C) at −0.9 V (vs. Ag/AgCl, in connection to a Pt wire counter electrode). This is followed by an electrodeposition of Au (1.5 C) from a gold plating solution (Orotemp 24 RTU RACK; Technic Inc.) at −0.9 V (vs. Ag/AgCl). Subsequently, platinum or platinum-CNT are deposited galvanostatically at −2 mA for 50 min from a platinum plating solution (Platinum RTP; Technic Inc.) or using a platinum plating solution containing various amounts (0.25-1.00 mg/ml) of CNT, along with 0.1 wt % Nafion and 2 mM 4-nitrobenzenediazonium tetrafluoroborate (NBD), respectively.

Such protocol to generate the Pt-CNT structure ensures uniform dispersion of CNT in the plating solution and hence a homogeneous loading of CNT within the Pt anode component 1510. This synthesis process results in bi-segment nanomotors with each component 1510, 1520 having a select length of approximately 1 µm for example.

To generate a control nanowire structure without the carbon-nanotubes 1514, Au/Pt—$Fe_3O_4$ nanowires are prepared by depositing the Pt—$Fe_3O_4$ component galvanostatically using the same conditions as for the Pt and Pt-CNT components from a platinum plating solution containing a suspension of $Fe_3O_4$—$(C_9H_{19}COOH)_2$ nanoparticles (0.5 mg/ml). The bilayer surfactant-coated iron oxide [$Fe_3O_4$—$(C_9H_{19}COOH)_2$] nanoparticles are synthesized by washing the nanoparticles thoroughly with deionized water and dried at 100° C. Nickel-containing nanomotors (Au/Ni/Au/Pt and Au/Ni/Au/Pt-CNT) are synthesized for the magnetically controlled experiments described below. Following the plating of the first gold segment (0.75 C), nickel is electrodeposited from a nickel plating solution [20 g L-1 $NiCl_2.6H_2O$, 515 g L-1 $Ni(H_2NSO_3).4H_2O$, and 20 g L-1 $H_3BO_3$ (buffered to pH 3.4)] at −1.0 V (vs. Ag/AgCl). A total charge of 0.5 C and 2.0 C are used for plating nickel for the 'racing' nanomotors and the speed-controlled nanomotors, respectively.

The second gold component (0.75 C) is then deposited, followed by the growth of the Pt or Pt-CNT component, as previously described. After depositing the nanomotors, the membrane is removed from the plating cell and rinsed thoroughly with nanopure water to remove all residues. The sputtered gold layer and the silver layer are simultaneously removed by mechanical polishing using cotton tip applicators soaked with 35% HNO3 for ca. 5 min to ensure complete silver dissolution. The bi-component nanowires are then released by immersing the membrane in 3 M NaOH for 30 min.

These nanowires are collected by centrifugation at 10,000 rpm for 5 min and washed repeatedly with nanopure water (18.2 MΩ) until a neutral pH is achieved. Between washing steps the nanowire solution is mixed and briefly sonicated (several seconds) to ensure the complete dispersion of nanowires in the washing water and hence the removal of salt residuals entrapped in the nanowire aggregate after centrifugation. Special attention is paid to the nanowires being washed directly before testing and suspended in freshly obtained nanopure water due to significant deceleration of the nanomotors speed in the presence of salt ions. All nanomotor solutions are stored in nanopure water at room temperature and their speed tested within a day of synthesis. The nanowires can be characterized using an FEI XL30 scanning electron microscope (SEM; from FEI Co., Hillsboro, Oreg.). The SEM is used to determine the length of each segment of the nanomotors.

The CNT incorporated nanomotor 1500 is designed to move in the presence of aqueous fuel solution that includes one or more redox species or substances that undergo redox reactions. The redox species or substances can include hydrogen peroxide ($H_2O_2$) based fuels, hydrazine based fuels, etc. In some implementations, the fuel solution can include various precursors to the redox species, such as glucose or sucrose. In particular, the environment in vivo includes glucose, sucrose and other biological substances that can be converted to $H_2O_2$ in presence of other substances such as enzymes. For example, glucose can be converted to $H_2O_2$ in the presence of glucose oxidase enzyme. In such implementations, the enzyme and the precursor substance can be found in the biological system. Alternatively, the enzyme can be incorporated onto the surface of the anode component 1510 or cathode component to promote conversion of glucose into $H_2O_2$.

The CNT incorporated nanomotor catalyzes the $H_2O_2$ based fuel to generate water and oxygen, for example. This $H_2O_2$ based fuel can also include a second redox specie or substance such as hydrazine to provide a synergistic increase of the speed of the nanomotor. The resulting Au/Pt-CNT nanowires 1500 can achieve average velocities of 94 µm/s with some nanowires traveling at speeds faster than 200 µm/s (equivalent to 100 body-lengths/second). This is several magnitudes faster than the speed achieved by CNT-free nanomachines. Further, the CNT incorporated nanowires can surpass speeds of most biological motors. The ultrafast motion of Au/Pt-CNT nanowires reflects the enhanced catalytic decomposition of the peroxide fuel on the Pt-CNT end.

In some implementations, other types of nanomotors can be used, such as swimmer nanomotors.

Functionalizing Nanomotor with Capture Probe

Figure 16:
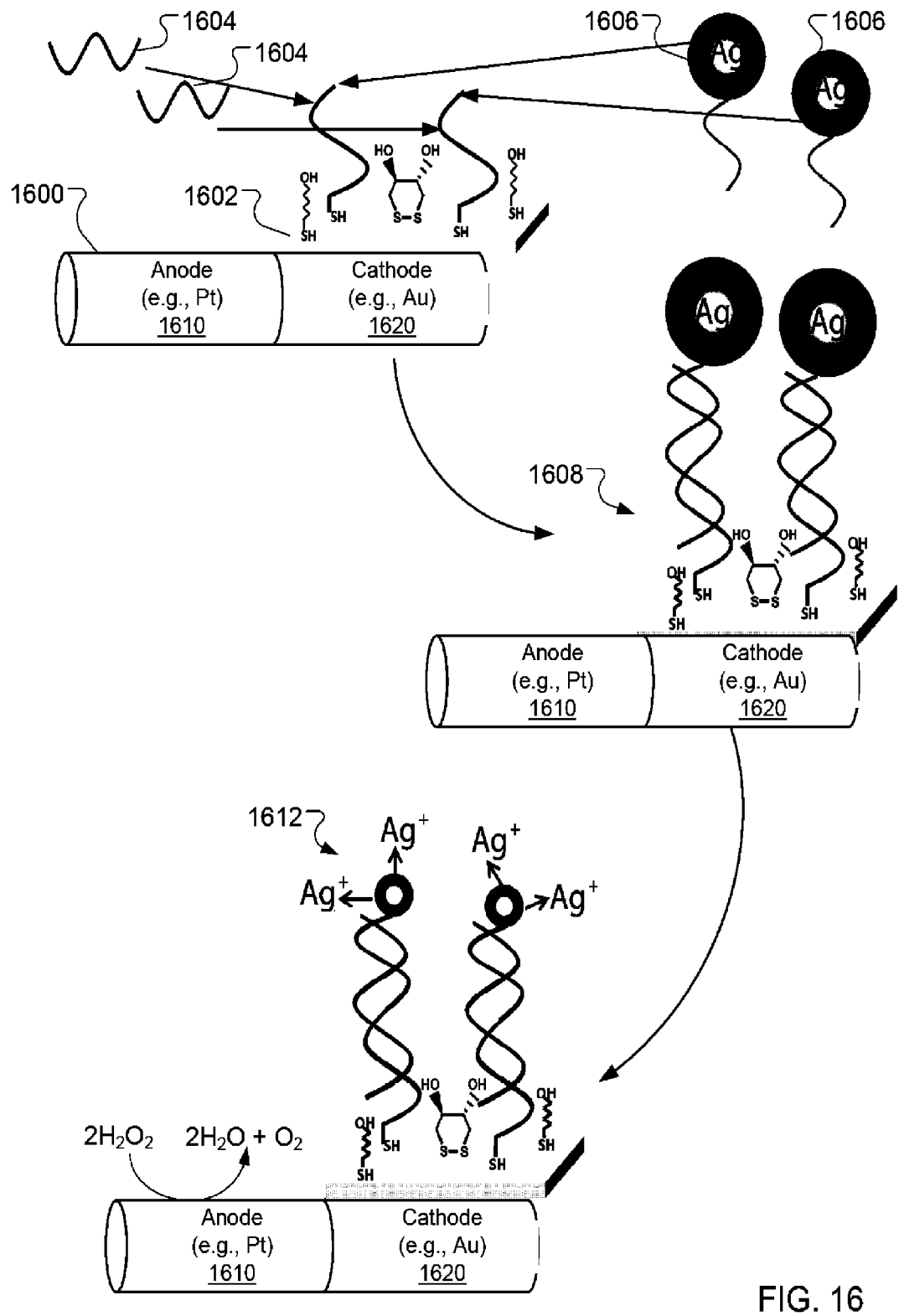
FIG. 16 is a block diagram showing an exemplary nanomotor functionalized with a capture probe for detecting DNA material.
Figure 17A:
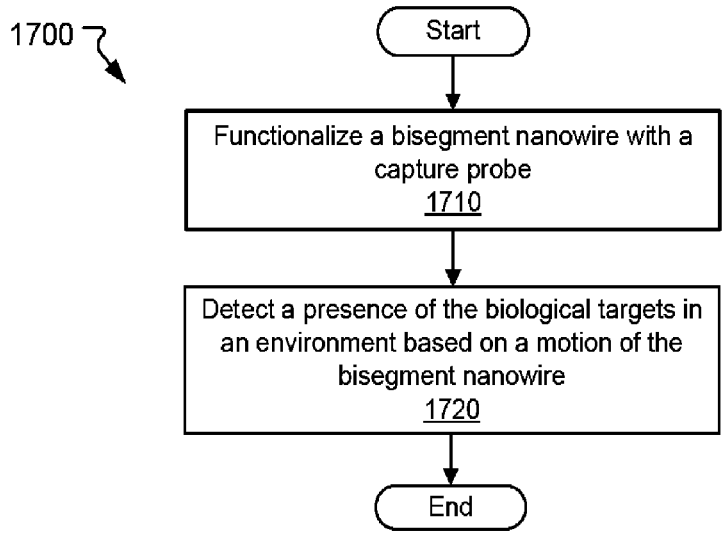
FIGS. 17A, 17B, 17C, 17D and 17E are process flow diagrams of an exemplary process for detecting biological targets based on motion of a nanowire.
Figure 17B:
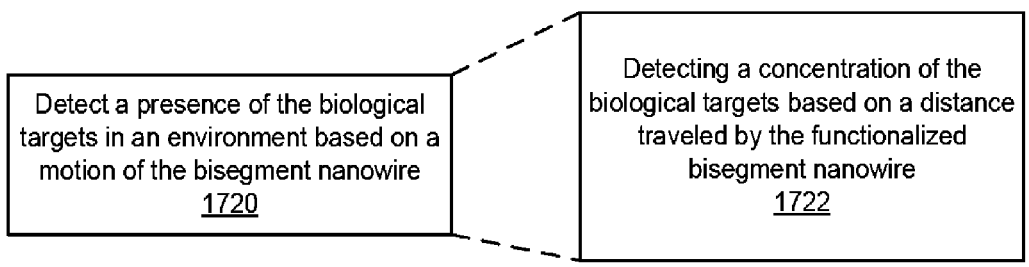
Figure 17C:
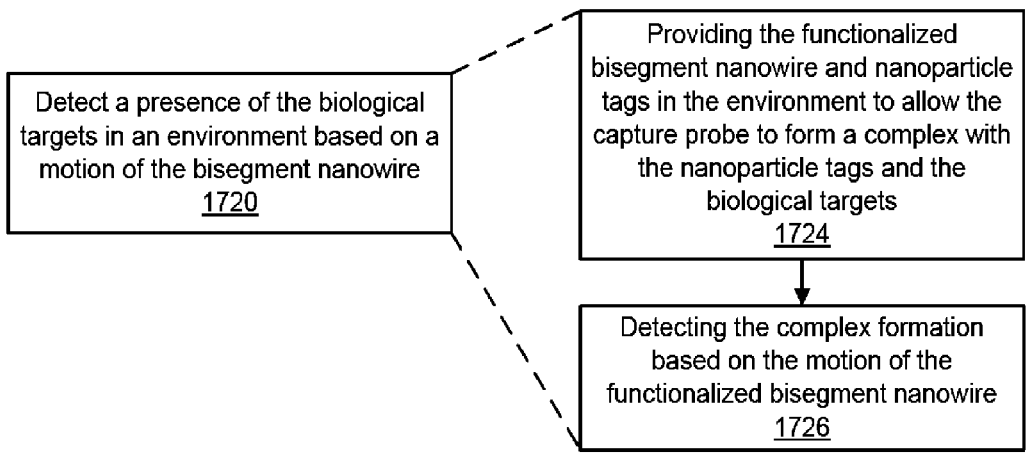
Figure 17D:
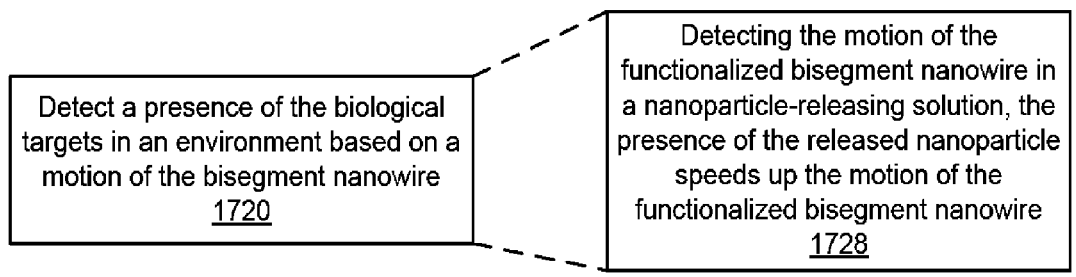
Figure 17E:
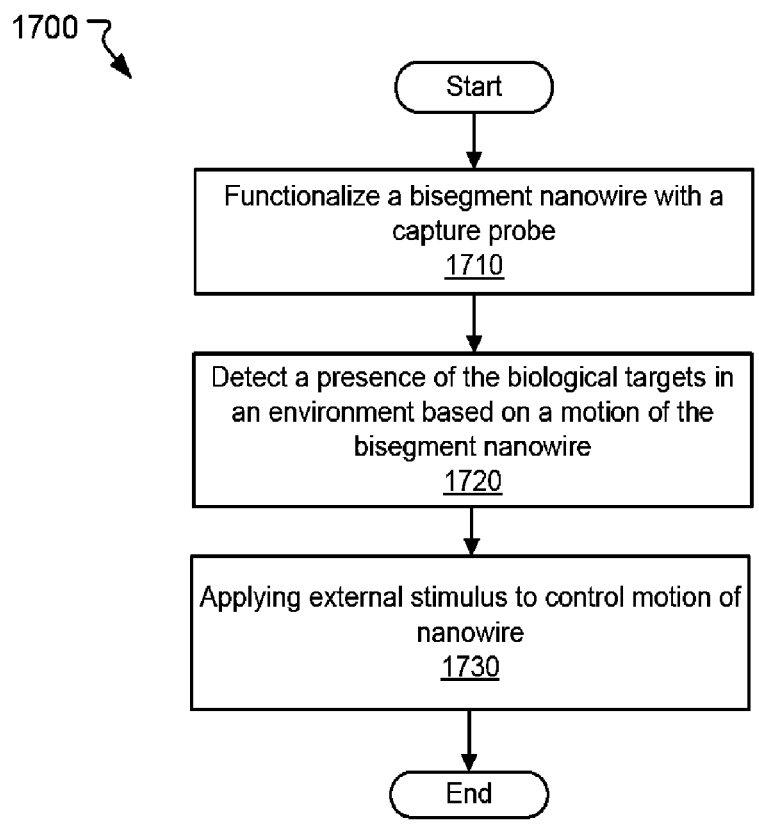

As described in FIGS. 4A, 4B and 4C above, FIG. 16 is a block diagram showing an exemplary nanomotor 1600 functionalized with a capture probe 1602 for detecting DNA material. For example, a cathode portion 1620 (e.g., gold electrode) is modified with a ternary monolayer composed of thiolated capture probe (SH-CP), mercaptohexanol (MCH) and dithiothreitol (DTT). When the nanomotor 1600 is in $Ag^+$ enriched solution (e.g., a solution with $Ag^+$ nanoparticles (NPs)), the presence of a complementary nucleic acid target 1604 in the solution leads to duplex formation 1608 and subsequent capture of silver nanoparticle tagged detector probe (SH-DP-Ag NPs) (1608). After a washing step to remove the excess unbound SH-DP-Ag NPs, the hydrogen peroxide fuel is added, leading to rapid dissolution of the captured nanoparticle tags into silver ions (1612). The $Ag^+$-enriched fuel is separated from the DNA bound to the gold electrode and directly added to an equal volume of freshly prepared nanomotor solution, thereby leading to a change of their speed and hence to concentration dependent nanomotor distance signals. Such signals can be easily and directly traced using optical microscopes, hence obviating the need for sophisticated analytical instruments. The movement of the nanomotor can be correlated to the DNA detection as described above.

In some implementations, other similar probes can be used to capture DNA, E. coli, or other biological materials.

FIGS. 17A, 17B, 17C, 17D and 17E are process flow diagrams of an exemplary process for detecting biological targets using nanoparticle induced nanowire motion. The process 1700 can include functionlizing a nanomachine with a capture probe (1710). The presence of biological targets in an environment can be detected based on a motion of the nanomachine (1720).

Detecting a presence of the biological targets in an environment based on a motion of the nanomachine can include detecting a concentration of the biological targets based on a distance traveled by the functionalized nanomachine (1722). Detecting a presence of the biological targets in an environment based on a motion of the nanomachine can include providing the functionalized nanomachine and nanoparticle tags in the environment to allow the capture probe to form a complex with the nanoparticle tags and the biological targets (1724). Detecting a presence of the biological targets in an environment based on a motion of the nanomachine can include Detecting the complex formation based on the motion of the functionalized nanomachine (1726). Detecting a presence of the biological targets in an environment based on a motion of the nanomachine can include detecting the motion of the functionalized nanomachine in a nanoparticle-releasing solution, the presence of the released nanoparticle speeds up the motion of the functionalized nanomachine (1728).

In some implementations, the method 1700 can include applying external stimulus to control motion of the nanowire (1730). Examples of external stimulus can include electromagnetic, thermal or electrochemical pulses.

The nanomachines can be implemented as a bisegment nanowire namotor as shown and described with respect to FIGS. 4A, 4B, 4C, 15A, 15B, 15C, and 16. In some implementations, the nanomachines can be implemented as other types of nanomotors including chemically-driven nanomotors and fuel-free nanomotors.

Thermal Modulation of Nanomotor Movement

Motion control is essential for various applications of man-made nanomachines. In this section, described is the ability to control and regulate the movement of catalytic nanowire motors by applying short heat pulses for allowing the motors to be accelerated or slow down. The accelerated motion observed during the heat pulses can be attributed to the thermal activation of the redox reactions of the hydrogen-peroxide fuel at the platinum and gold segments and to the decreased viscosity of the aqueous medium at elevated temperatures. The thermally-modulated motion during repetitive temperature 'On/Off' cycles is highly reversible and fast, with speeds of 14 and 45 μm/s at 25 and 65° C., respectively. A wide range of speeds can be generated by tailoring the temperature, to yield a linear speed-temperature dependence. Through the use of nickel-containing nanomotors, we also demonstrate the ability to combine the thermally-regulated motion of catalytic nanomotors with magnetic guidance. Such on demand control of the movement of nanowire motors holds great promise for complex operations of future man-made nanomachines and for creating more sophisticated nanomotors.

Man-made nanomotors can use propulsion of asymmetric (bisegment) nanowires in the presence of a chemical fuel (commonly hydrogen peroxide). The underlying mechanisms for the self-propulsion of bimetallic catalytic nanomotors can include electrokinetic self-electrophoresis and the oxygen bubble's formation. Both of these mechanisms are associated with the electrocatalytic decomposition of the peroxide fuel. The autonomous motion of these chemically-powered nanomachines can have various applications, ranging from nanoscale transport and distribution to nanosurgical operations. The speed and power of catalytic nanomotors can be obtained by judicious control of the nanowire or fuel composition. Precise motion control also can be possible for synthetic nanomotors. Regulating on demand the movement of nanomotors can provide additional applications. Magnetically-directed movement of nanowire motors can be accomplished through the incorporation of a ferromagnetic (nickel) segment. This allows for magnetic guidance and steering in the presence of an external magnetic field, as well as a 'stop-and-go' operation through a modulated magnetic field. Such response to changes in the local environment can be used to control the operation of artificial functional nanomotors.

Described herein is temperature-modulated motion of catalytic nanomotors achieved by applying short heat pulses. Temperature-dependent electrochemical processes involves the use of electrically heated electrodes for enhanced electrochemical measurements through accelerated kinetics of redox processes and/or increased rates of mass transport. Illustrated below are analogous high temperature propulsion of catalytic nanomotors and the use of heat pulses for regulating on demand the motion of such nanowire motors. Unlike hot wire electrochemistry where the wire serves as the heated working electrode, the heated wire acts here solely as the heat source for controlling the solution temperature in the plane of the nanomotors. Such use of heat pulses can lead to a thermal modulation of the movement of artificial nanomotors, with a fine, reversible and rapid control of the nanomotor velocity. Also described is the coupling of the new thermally-regulated motion with magnetic guidance towards a more advanced temporal and spatial motion control.

On-Demand Reversible Thermal Modulation of the Nanomotor Movement

Figure 18:
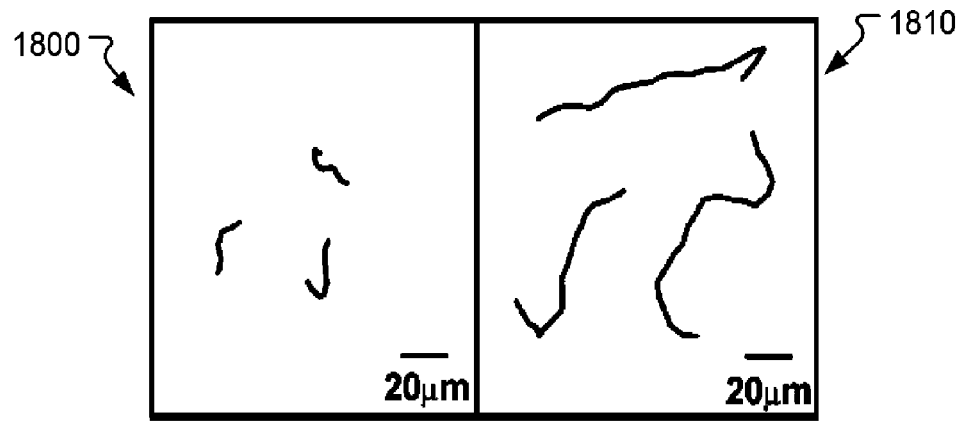
FIG. 18 shows high temperature electrochemical propulsion. Tracking lines of nanomotors illustrating the distances traveled by three Au—Pt nanowires at room temperature (left panel) and at an elevated temperature of 65° C. (right panel) using a 5 wt % $H_2O_2$ fuel solution. The elevated temperature was obtained by using a heating current of 600 mA with the gold-coated platinum wire located 30 μm above the plane of the nanomotors. The temperature refers to the focal plane of the nanomotors.

FIG. 18 illustrates the accelerated velocity of catalytic nanomotors associated with the high-temperature electrochemical propulsion. It compares traces of three Au—Pt nanomotors, taken from videos of the nanowires in the presence of the peroxide fuel using room temperature (1800) and elevated temperature (1810) over a 2 second period. The heat source (a 25 diameter μm Au-coated Pt wire) was placed 30 μm above the plane of the nanomotors, leading to a temperature of 65° C. in that plane (in connection to a DC heat current of 600 mA). The nanowires exposed to the elevated temperature travel substantially (~3 fold) longer distances than the 'room-temperature' motors over the same time period (average distance of 90 vs. 28 μm). Such distances correspond to speeds of 45 and 14 μm s$^{-1}$ for the elevated and room temperatures, respectively. The increased speed is attributed to the accelerated kinetics of the redox reactions of the peroxide fuel (on both segments) and to a lower solution viscosity (and hence diminished friction forces) with the rising temperature (see discussion below). In view of a microscale convection around hot-wire electrodes, a control experiment, performed without the peroxide fuel, examined potentially disturbing convective effects at the elevated temperature. This revealed almost no self-propelled non-Brownian motion, with only a slight drift due to a weak thermal convection (3 μm s$^{-1}$; not shown). Apparently, the self-propelled nanomotors are not prone to convection effect (in presence of the fuel), provided that they are kept on the surface of the microscopic glass slide (placed at a distance larger than 20 μm from the heat source).

Figure 19:
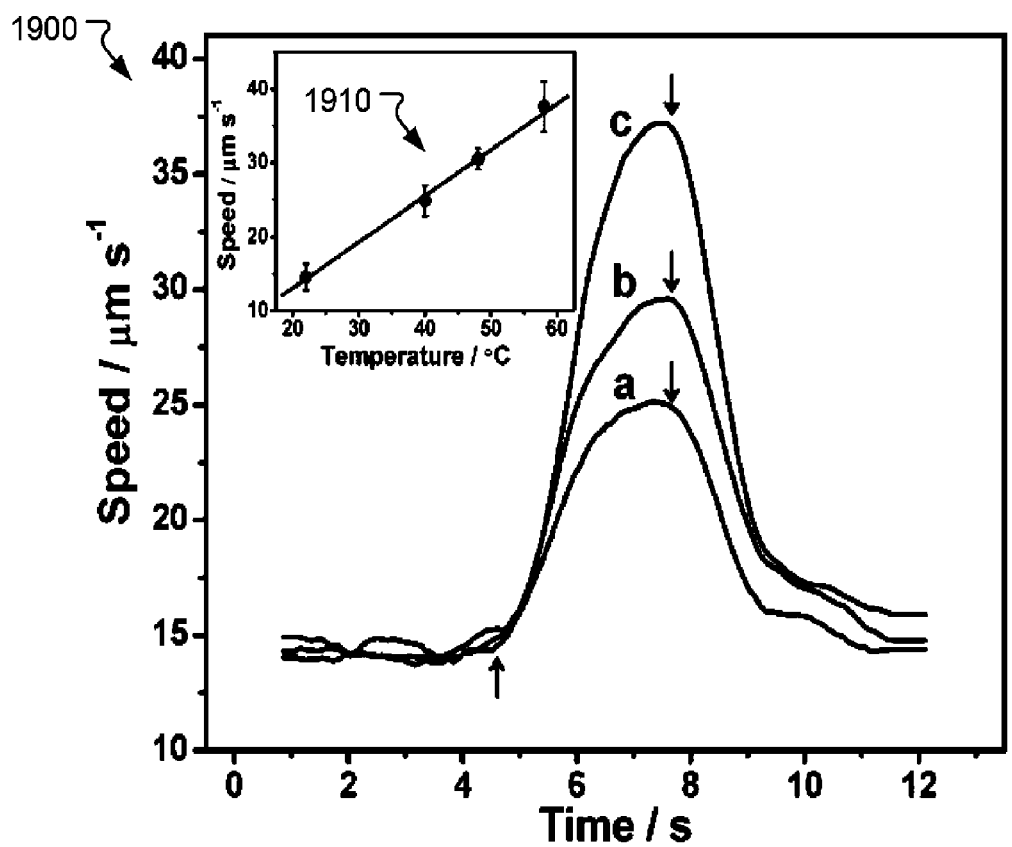
FIG. 19 shows speed-time profiles of Au—Pt nanomotors during different 3-sec heat pulses to 40 (a), 48 (b) and 58 (c)° C. in a 5 wt % $H_2O_2$ solution. The arrows (around 5 and 8 sec) correspond to the time of switching the heating current 'on' and 'off', respectively. Data shown represent the average speed of 60 nanomotors. Raw data have been smoothed using Fast Fourier Transformation (Origin software; 5 points). Inset displays the linear relationship between the nanomotor speed and the temperature. Temperatures refer to the focal plane of the nanomotors. The error bars correspond to standard deviations, calculated on the basis of 4 nanomotor tracks.

The high-temperature electrochemical propulsion offers a fine and reversible control over the nanomotor velocity. FIG. 19 examines the influence of different temperature pulse amplitudes upon the nanomotor speed in a 5 wt % peroxide solution. It displays speed-time profiles 1900 for 3-sec temperature pulses to 40 (a), 48 (b), and 58 (c)° C. (in the plane of the observed nanomotors). In all three cases, the speed increases rapidly with the time at first, leveling off towards the end of the pulse, reaching maximal values of 25, 31, and 38 μm s$^{-1}$ at 40, 48, and 58° C., respectively. Similarly, a sharp decrease in the velocity is observed upon switching the heat off, approaching the original ('cold') value within 10 sec. Such speed profiles reflect the temporal heat formation and cooling down process during the heat pulse and are consistent with earlier temperature profiles during short heat pulses (also at 25 μm diameter Pt wire). The spread of heat in the solution surrounding the hot wires and the corresponding temperature profiles have been calculated numerically. For example, an 80° C. wire surface temperature corresponds to a solution temperature of 50° C. at a 40 μm distance below the wire center. Different solution temperatures (at the nanomotor plane) have been estimated in a similar fashion for different heating currents and source-plane distances for both platinum and gold wires. The data of FIG. 19 indicate that a wide range of nanomotor speeds can be generated through a fine control of the temperature. Indeed, the inset 1910 of FIG. 2 illustrates a linear relation between the temperature and the nanomotor speed over the 14 to 37 μm s$^{-1}$ range (slope, 0.635 μm s$^{-1\,\circ}$ C$^{-1}$). Such linear relation between the temperature and the nanomotor speed is somewhat surprising in view of the complex temperature-dependent processes and opposing thermal effects (discussed below).

Figure 20:
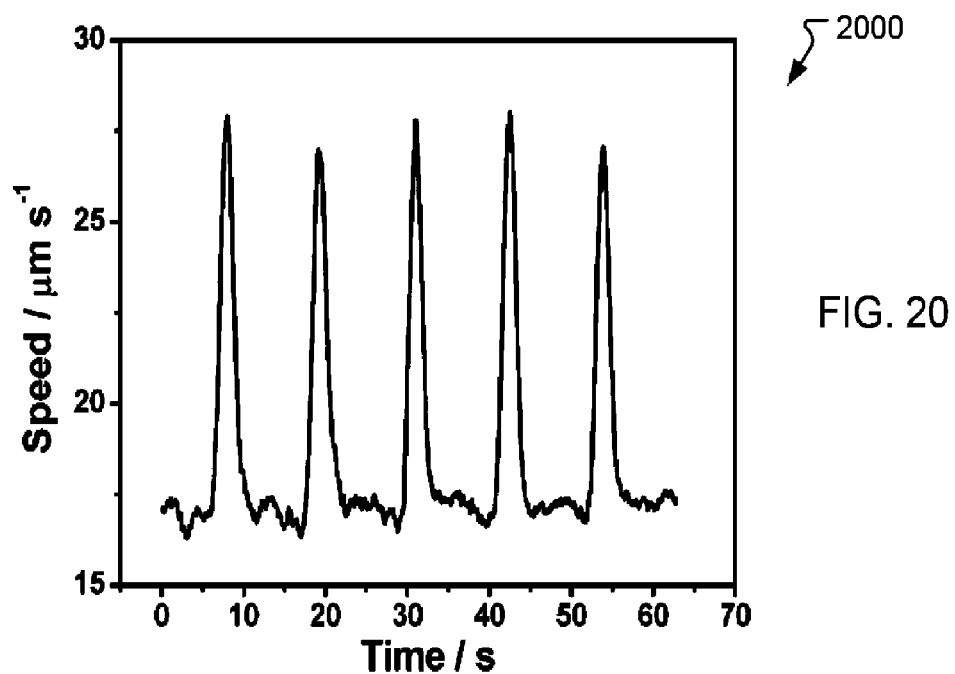
FIG. 20 shows modulated motion of catalytic nanomotors during five 1.5 s heat pulses (corresponding to a temperature of 50° C.), at 11.5 sec intervals. Data shown represent the average speed of 3 nanomotors. The elevated temperature was obtained by using a heat current 700 mA with the gold wire located 35 μm above the plane of the nanomotors. Data processing is as in FIG. 19.

The speed-temperature profiles 1900 of FIG. 19 indicate an ability to regulate on demand the motion of catalytic nanowire motors in connection to an external 'On/Off' temperature switch. A dramatic speed acceleration from 11 to 37 μm s$^{-1}$ and slowing down back to 12 μm s$^{-1}$ can be observed during this 4 sec temperature pulse. Such ability to modulate thermally the motion of catalytic nanomotors is illustrated also using the five short (1.5 s) heat pulses 2000 (corresponding to a temperature of 50° C.) at 11.5 s intervals of FIG. 20. Reversible changes in the speed of the Pt-Au nanomotor (between 17 and 28 μm s$^{-1}$) are observed during these repetitive heating and cooling periods. Due to the short duration of the heat pulse (1.5 sec), the nanomotors are not reaching their maximal steady-state speed value. Depending on the heating current, it can take up to 2 sec for the system to reach a thermal steady state. Therefore, temperatures lower than the steady-state value are expected using the short heat pulses of FIG. 20 compared to long pulses (e.g., FIG. 19) or use of continuous heating (e.g., FIG. 18, Graph 1810). Such modulated motion can be repeated continuously and reversibly, indicating negligible fuel depletion in the plane of the nanomotors (as expected from the small voltage drop along the heated wire and its distance to the nanomotor plane). Similar switching of the movement of biological motors can be obtained, including a temperature-induced acceleration of the biomotor actomyosin and a light-induced modulated speed of kinesin in connection to the controlled release of its ATP fuel. These biomotors respond slowly (within few min) to these external stimuli, as compared to the instantaneous (sec) thermal 'switching' of the present synthetic nanomotor system.

Figure 21A:
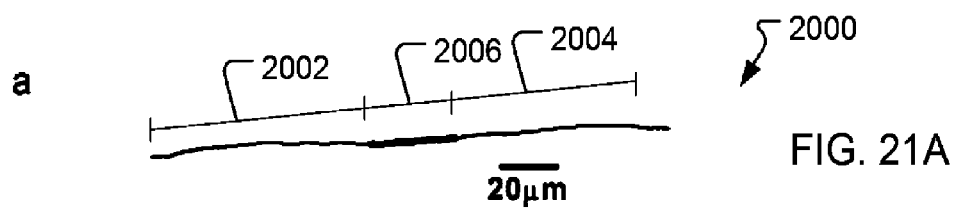
FIG. 21A shows high-temperature propulsion of magnetically guided Ni-containing nanomotor during two 3 s heat pulses with an intermittent OFF period of 3 sec. Gold heating wire (25 μm diameter) is placed at 30 μm distance from the plane of the nanomotors.
Figure 21B:
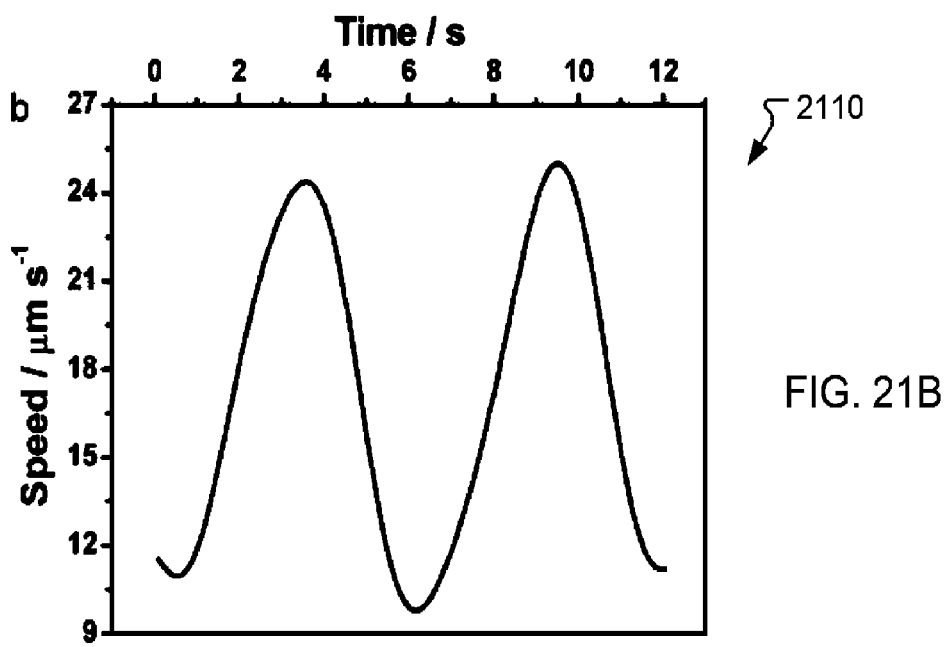
FIG. 21B shows speed-time profile corresponding to FIG. 21A. Data processing is as in FIG. 19.

A directed motion of the thermally-stimulated nanomotors (essential for diverse applications) has been accomplished by incorporating a ferromagnetic nickel segment and aligning the magnetized nanowires using an external magnetic field. FIG. 21A demonstrates the ability to combine the thermally-regulated motion of catalytic nanomotors with such magnetic guidance. It depicts the speed modulation during two 3 s heat pulses to 50° C. (2002 and 2004) with an intermittent off period (2006) of 3 s while aligning the Au—Ni—Pt nanowire in a relatively straight line under a weak magnetic field. The dramatic speed acceleration during the heat pulses 2002 and 2004 is indicated from the 2.5-fold larger displacement of the nanomotor (vs. the path observed during the intermittent 3 sec 'cooling' period; 2006). The slight deviation from the straight line during the pulses reflects the negligible thermal convective drift (discussed earlier). The corresponding temperature-time profile 2110 shown in 21b indicates that the speed increases rapidly upon applying the heat pulse, reaching a maximal value of 25 μm s$^{-1}$, and decreases sharply back to 10 μm s$^{-1}$ during the cooling period. Similarly, it would be possible to combine the accelerated motion with magnetic steering at different directions at preselected locations and times, as well as with a magnetic loading and unloading of cargo. Such coupling of magnetic guidance with an on-demand thermal motion control leads to a more advanced (spatial and temporal) motion control and holds great promise for performing demanding tasks and creating more sophisticated nanomotors.

Temperature Effect upon the Kinetics of Electrochemical Processes of the Fuel

Figure 22:
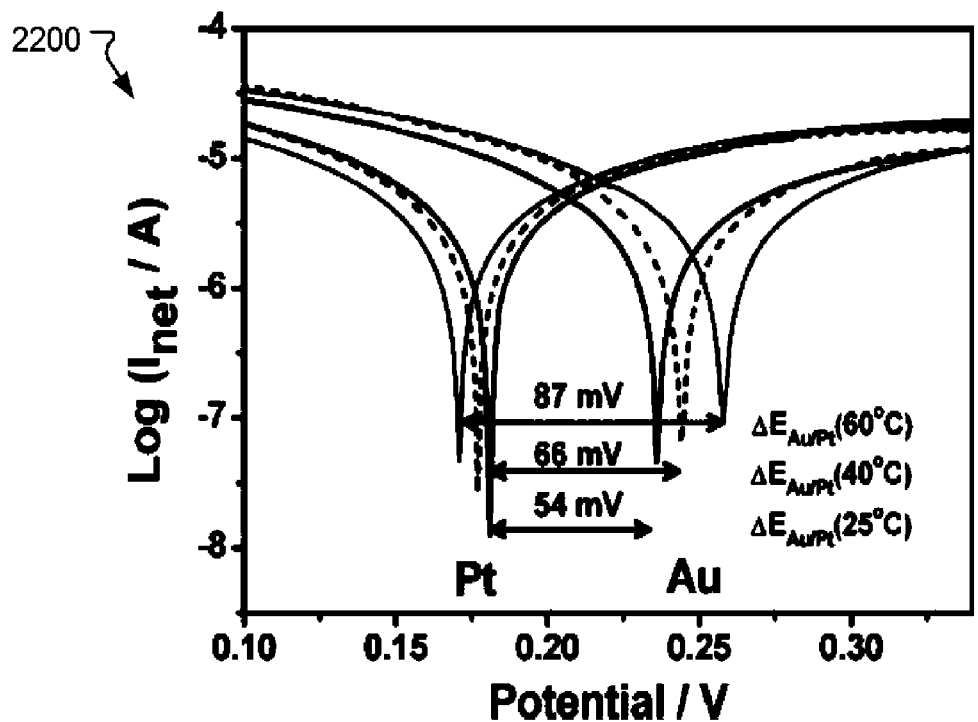
FIG. 22 shows Tafel plots at Pt and Au disk electrodes in a 5 wt % $H_2O_2$ solution at different temperatures. The mixed potential differences (ΔE, Pt vs. Au) are also indicated in the figure. Reference electrode: Ag/AgCl (3 M NaCl).

Tafel plots were used to examine the thermal activation of the electrochemical processes of the peroxide fuel at the platinum and gold segment materials and temperature-induced changes in the mixed potential difference (ΔE) of the fuel at the corresponding materials. FIG. 22 depicts such plots 2200 for the hydrogen peroxide reaction at Pt and Au disk electrodes using solution temperatures of 25, 40 and 60° C. Gradual potential shifts from 181 to 171 mV (Pt) and from 236 to 258 mV (Au) are observed upon raising the temperature from 25 to 60° C. Such plots indicate a thermally-induced accelerated kinetics of both the oxidation and reduction reactions of the peroxide fuel. Such thermal activation is indicated also from the increased current densities (at both electrodes) upon raising the temperature. The larger potential shift observed at the gold electrode indicates that the temperature effect is more pronounced for the cathodic reaction at this material. This is consistent with the larger temperature-induced acceleration of reaction processes with higher activation energy. The self-electrophoresis mechanism of asymmetric nanowire motors suggests that the speed of such nanomotors is proportional to the mixed potential difference (ΔE) of the fuel at the corresponding segment materials. Indeed, the opposite potential shifts observed at the Pt and Au electrodes upon raising the temperature lead to larger ΔE values of 66 and 87 mV (at 40 and 60° C., respectively), compared to the 54 mV value of the room temperature (FIG. 22). Such increase of the ΔE value with the temperature is consistent with the speed-temperature profile of FIG. 19. The oxygen bubble's formation propulsion mechanism, which also involves the electrochemical decomposition of the fuel, can also explain the observed nanomotor acceleration on the basis of such temperature-induced activation of the electrochemical fuel reactions.

While FIG. 5 indicates that the accelerated motion observed at elevated temperatures reflects the thermal activation of the electrochemical reactions of the hydrogen-peroxide fuel, one should consider other thermal effects influencing the nanomotor movement. In particular, the dynamic viscosity ($\mu$) of water decreases in a non-linear manner by ca. 50% upon increasing the temperature from 20 to 55° C. and this is expected to double the velocity v of the nanomotor (assuming that $F_D$, the frictional force in Stokes law, is constant). In practice, the propulsion force $F_P$ (same value, opposite direction compared to $F_D$) should also increase with the temperature due to the accelerated reaction kinetics at the nanomotor surface. In contrast, raising the temperature increases the solution conductivity as well as the autoprotolysis of water, and these changes are expected to lower the nanomotor speed. While some of the above thermal effects compensate each other, the net result is a dramatic enhancement of the nanomotor motion upon applying the heat pulses, and a (somewhat surprising and coincidental) linear dependence between the speed and the temperature (FIG. 19, inset 1910).

Various implementations have been described of a novel approach for modulating and activating thermally the motion of catalytic nanomotors. Such reversible thermal control represents a novel approach for regulating on-demand the operation of artificial nanomotors. Although the exact mechanism for the propulsion of fuel-driven catalytic nanowire motors is still not fully resolved the observed thermally-modulated speed appears to reflect primarily heat-induced changes in the kinetics of the fuel redox processes and of the solution viscosity. Indeed, the new data further support the role of the electrochemical processes in the observed motion of catalytic nanowires. Such thermal modulation of the movement of artificial nanomotors holds great promise for diverse future applications of functional man-made nanomachines. For example, it would be possible to incorporate multiple heated wires in different locations within a microfabricated channel network for providing an on demand (spatial and temporal) activation of a nanoscale transport system.

Experimental Section

The bi-segment nanomotors were prepared by sequential electrodeposition of the gold and platinum segments into a porous alumina membrane template (Catalog no. 6809-6022; Whatman, Maidstone, U.K.). The branched side of the membrane was initially sputtered with gold. A sacrificial silver layer of total charge of 2 C was electrodeposited using a commercial silver plating solution (1025 RTU@4.5 Troy/Gallon; Technic Inc., Anaheim, Calif.) at a potential of −0.9 V (vs. Ag/AgCl (3 M NaCl), in connection to a Pt wire counter electrode. Subsequently, Au (1.5 C) was electrodeposited at −0.9 V from a gold plating solution (Orotemp 24 RTU RACK; Technic Inc., Anaheim, Calif.). Platinum was then deposited galvanostatically at −2 mA for 50 min from a platinum plating solution (Platinum RTP; Technic Inc). Similarly, magnetic nanomotors were synthesized by introducing ferromagnetic nickel segment (Au/Ni/Au/Pt). A total charge of 0.5 C of nickel was electrodeposited from a plating solution [20 g L$^{-1}$ NiCl.6H$_2$O], 515 g L$^{-1}$ Ni(H$_2$NSO$_3$) .4H$_2$O, and 20 g L$^{-1}$ H$_3$BO$_3$ (buffered to pH 3.4)] at −1.0 V (vs. Ag/AgCl). The sputtered gold layer and the sacrificial silver layer were removed simultaneously by rubbing with 35% HNO$_3$ for ca. 3 min to ensure complete silver dissolution. The membrane was then dissolved in 3 M NaOH for 30 min to completely release nanowires. These nanowires were collected by centrifugation at 10,000 rpm for 5 min and washed repeatedly with nanopure water (18.2 MΩ·cm) until a neutral pH was achieved. All nanowire solutions were stored in nanopure water at room temperature and their speed was tested on the same day of synthesis.

An epoxy well embedded with a gold-coated platinum wire or a gold wire (25 μm diameter) was prepared on a microscope glass slide to study the effect of temperature on the nanomotor speed. While both gold and platinum can be used as materials for the heating wire, the platinum was coated with a dense gold film to suppress spontaneous catalytic decomposition of the fuel. The wire was not stretched straight to provide different source-plane distances in connection to a fine x-y-z setting. To measure the distance between the heated wire and the surface of the microscope slide (where the nanomotor movement was monitored), we relied on the micrometer screw on the microscope's x-y-z stage, calibrated using a short gold wire with a 200 μm diameter. A diluted nanomotor suspension was added to the epoxy well and mixed with a freshly prepared hydrogen peroxide solution to obtain a final 5% (w/v) concentration. The real time movement of nanomotors was recorded at room temperature and elevated temperatures. Higher temperatures were realized by applying pre-determined currents through the heating wire. The heating current was provided by a DC power supply (Agilent E3645A). A logic module (Model "LOGO! 230RC", Siemens AG, Berlin, Germany) was used as a programmable relay to apply the temperature pulses, as was described earlier.

Tracking of nanomotors was performed following the protocol reported earlier. Briefly, an inverted optical microscope (Nikon Instrument Inc., Eclipse TE2000-S) equipped with a 20× objective, a Photometrics CoolSnap CF camera (Roper Scientific, Duluth, Ga.) and a MetaMorph 7.1 software (Molecular Devices, Sunnyvale, Calif., USA) were used for capturing movies at a frame rate of 10 frames per second. The depth of the field was very small (ca. 2 μm), and only the nanomotors on the glass surface were brought into the focal plane. The nanomotor movement was tracked using Metamorph tracking module and the results were analyzed using Origin Pro 7.5 software. The data were smoothed using in-built smoothing functions in Origin Pro 7.5.

Tafel plots were used to obtain the mixed potential established at the gold and platinum electrode materials in a 5 wt % hydrogen peroxide solution. Gold and platinum disk electrodes (CH Instruments, Austin, Tex.) were used as the working electrode in these electrochemical measurements. Cyclic voltammetry of 5 wt % aqueous hydrogen peroxide (without any electrolyte) was performed using the CH Instrument Model CHI630C at a scan rate of 50 mV s$^{-1}$ and over a potential range of 0.1 to 0.4 V (vs. Ag/AgCl), along with platinum wire as a counter electrode. Further details were given earlier.

Estimation of Nanomotors' Temperature.

Estimation of the temperature in the plane of the nanomotors was based on earlier simulations of the temperature profile around a heated wire (25 μm diameter) in vertical and horizontal orientations. We relied on FIG. 19 in ref. 6 to estimate the temperature beneath the heated wire. The temperature of the surrounding fluid depends on the distance from the wire surface. Based on the simulations of Beckmann et al. and earlier temperature calibrations for 25-μm Pt and Au wires, we interpolated temperature values for different heating currents between 0 and 900 mA and heat-source distances ranging from 15 to 70 μm. We further assume a negligible change in the bulk temperature (of the entire fluid volume) during our short (1.5-3.0 s) heat pulses and their 10-12 s intermittent cooling periods. Such assumption is supported by the following calculation. For example, a heat (Q) of 0.8625 J can be calculated for a 3 s pulse using a 500 mA heating current (I) and a resistance (R) of 1.15Ω (measured for the Pt wire), based on $Q=t \cdot R \cdot I^2$. Considering a 200 μL bulk volume and the heat capacity of water (4186 J kg$^{-1}$ K$^{-1}$), we can expect that such pulse will lead to a maximum increase in the bulk temperature of 1.03 K. On the other hand, heat is removed constantly from the fluid due to thermal conductivity of the glass slide. Hence, we assume that the bulk temperature remains stable during a multi-pulse experiment over 30 to 60 s periods.

Electrochemically-Triggered Motion of Catalytic Nanomotors

Locomotion of nanoscale objects through a fluid environment is described. For example, catalytic nanowire motors can exhibit autonomous self propulsion in the presence of a $H_2O_2$ fuel. Also, chemically-powered nanowire motors can provide motion along with a cargo-towing force. These capabilities of synthetic nanomotors can have various application sin nanoscale transport and assembly.

The ability of nanomotors to perform complex operations requires a precise spatial and temporal control of their motion. Reversibly starting and stopping artificial nanomotors and regulating their movement on demand remain a major technological challenge. Such motion control can be imparted onto catalytic nanomotors by using magnetic guidance and rapid thermal acceleration.

Described in this section are techniques, apparatus and system for implementing electrochemically-controlled movement of catalytic nanomotors. Both a cyclic 'on' and 'off' electrochemical activation of the nanomotor motion as well as fine speed control are illustrated by placing a gold-fiber working electrode in close proximity to the plane of the nanomotors and applying different potentials. The described electrochemically-controlled movement of catalytic nanomotors involves electrolytic reactions of the $H_2O_2$ and $O_2$, and reflects primarily the role of the oxygen generated and consumed at these potentials. Such reversible voltage-driven motion represents an attractive approach for on-demand regulation of artificial nanomotors and opens the door to new and exciting operations of these nanoscale devices.

Figure 23:
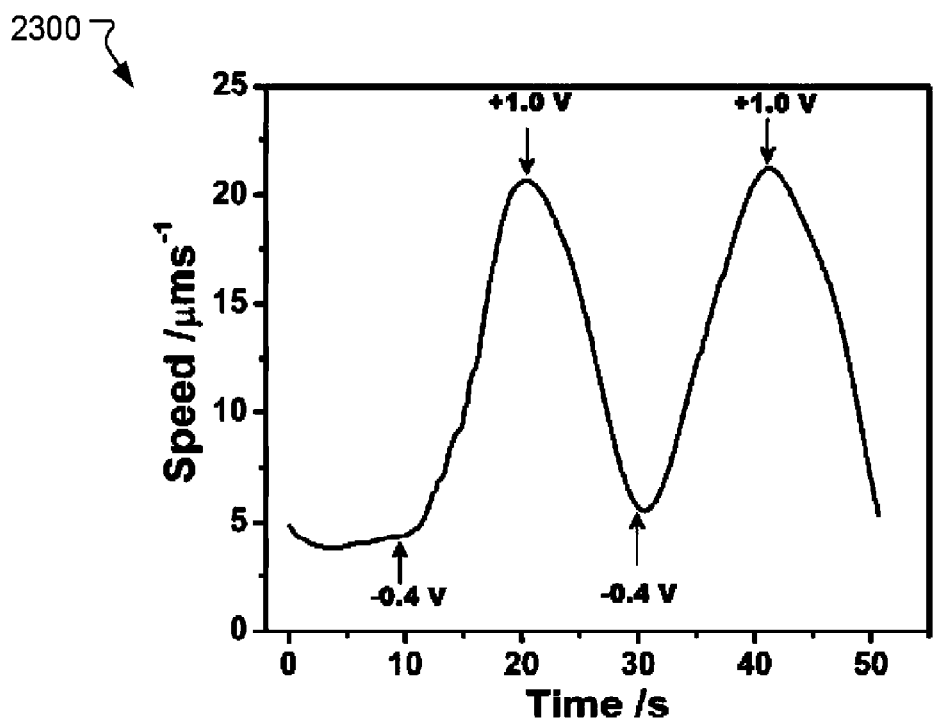
FIG. 23 shows cyclic 'on' and 'off' electrochemical activation of the nanomotor motion upon switching the applied potential (+1.0 to −0.4 V, indicated by arrows) at 10 s intervals in a 5 wt % $H_2O_2$ solution.

The ability to use potential control for reversibly starting and stopping the motion of catalytic nanomotors is illustrated in FIG. 23. It displays velocity-time profiles 2300 for 10-sec potential pulses of +1.0 and −0.4 V (vs. Ag|AgCl|100 mM KCl reference) in a 5 wt % $H_2O_2$ fuel solution. A dramatic speed acceleration, from 4 to 22 μm s$^{-1}$ is observed upon stepping the potential from +1.0 V to −0.40 V. The nanomotor speed decreases rapidly upon switching the potential back to +1.0 V, reaching a value of 5 μm s$^{-1}$ (down to Brownian motion) within 10 sec. The speed of these nanomotors without an applied potential corresponded to 9 μm s$^{-1}$ (not shown), which is characteristic to Pt—Au nanowire motors. The cyclic 'on/off' electrochemical modulation of the nanomotor motion can be repeated several times.

Figure 24:
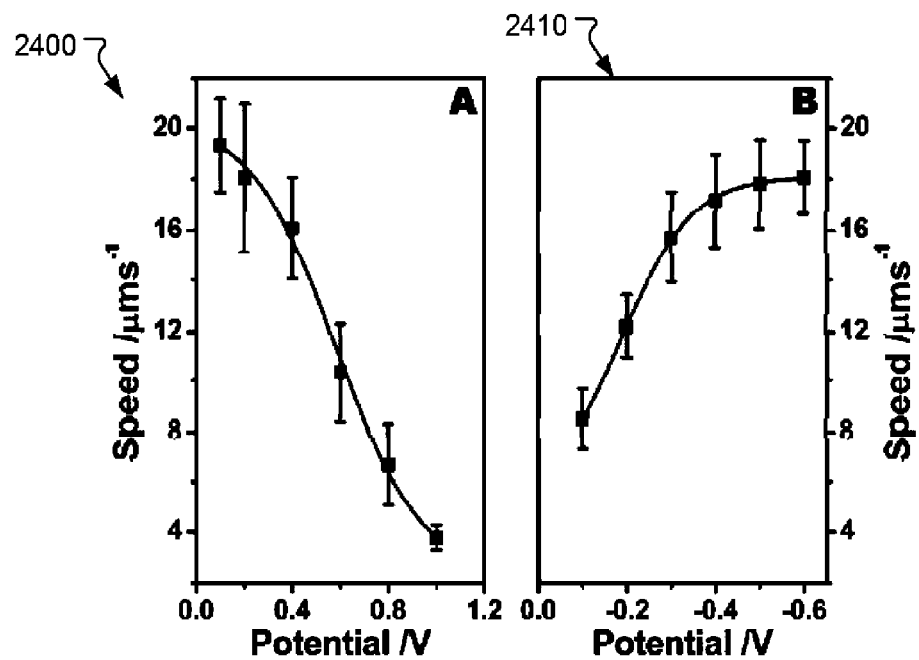
FIG. 24 shows Speed-potential profiles of Au—Pt nanomotors in a 5% $H_2O_2$ solution. Nanomotor (n=30) speed upon stepping the potential from −0.4 V to different positive potentials (0.1, 0.2, 0.4, 0.6, 0.8 and 1.0 V) (left panel);and +1.0 V to different negative potentials (−0.1, −0.2, −0.3, −0.4, −0.5 and −0.6 V) (right panel).

In addition to a reversible 'on' and 'off' switching of the nanomotor motion, it is possible to tune the applied potential for regulating the movement of catalytic nanomotors. Such potential-dependence of the nanomotor speed is illustrated in FIG. 24. Stepping the potential from −0.4 V to different positive potentials leads to a gradual decrease of the speed from nearly 20 μm s$^{-1}$ to 16, 10 and 4 μm s$^{-1}$ (at +0.40, +0.60 and +1.0 V, respectively; FIG. 24, panel A 2400). Similarly, stepping the potential from +1.0 V to different negative potentials results in a gradual rise in the speed from 5 pμs$^{-1}$ to 8, 12 and 16 μm s$^{-1}$ at −0.10, −0.20 and −0.30 V, respectively, with a leveling off around 18 μm s$^{-1}$ for potentials more negative than -0.40 V (FIG. 24, panel B 2410).

The speed-potential profiles of FIG. 2 reflect several redox reactions of electroactive substances in the bulk solution, and particularly of the $H_2O_2$ fuel and dissolved $O_2$ involved in the nanomotor movement. Such reactions were evaluated using linear-sweep voltammetry at the gold-fiber electrode, in the presence and absence of $H_2O_2$ and dissolved $O_2$. These experiments confirmed that the reduction processes of $O_2$ and $H_2O_2$ start at potentials more negative than −0.1 V and +0.1 V, respectively, with the oxygen displaying a peak potential of −0.4 V (not shown). The oxygen reduction signal was substantially smaller than the peroxide one, reflecting their vastly different concentrations in bulk (1.5 M peroxide vs. 1 mM oxygen).

The voltammetric response of oxygen correlates well with the speed profile of FIG. 24, panel B (2410), indicating that the reduction of oxygen is the primary reason for the accelerated motion observed at negative potentials. Scanning the potential of the gold fiber electrode in the anodic direction led to a growing $H_2O_2$ oxidation current, starting around +0.40 V (not shown). Due to the large excess of $H_2O_2$, such peroxide oxidation process leads to a dramatic increase in the localized oxygen concentration up to the saturation level. In contrast, the oxygen reduction (generating $H_2O_2$) has a negligible effect upon the overall peroxide concentration.

Additional data indicate that changes in the oxygen level are responsible for the observed motion control. For example, the Au—Pt nanomotors traveled substantially longer distances upon removing the oxygen from the fuel solution compared to distances observed in an oxygen-saturated atmosphere. Such distances corresponded to speeds of 20 and 4.6 μm s$^{-1}$ for the argon and oxygen atmospheres, respectively. Nearly identical distances, corresponding to speeds of 22 and 4.0 μm s$^{-1}$, were observed in analogous controlled-potential experiments at −0.40 and +1.0 V, respectively.

The effect of oxygen concentration upon the nanomotor motion can be explained in different ways, considering the different mechanisms for the propulsion of catalytic nanomotors. One of the most promising explanation relies on the self-electrophoresis mechanism for explaining the observed behavior. Tafel plots for the peroxide fuel (commonly used in connection to this mechanism), recorded in the presence of oxygen, argon and air, suggest that the changes in the oxygen level affect primarily the anodic reaction on the Pt segment. While the mixed potential of the Au electrode is nearly independent upon the presence of oxygen, the potential of the Pt electrode gradually shifts from 194, to 188 and 181 mV in the presence of oxygen, air and argon atmospheres, respectively. These potential shifts lead to larger values of the mixed potential difference $\Delta E_{Au/Pt}$ from 41 mV using oxygen to 55 mV under argon, compared to 50 mV for the air atmosphere. Such trend in the $\Delta E_{Au/Pt}$ values is consistent with the observed nanomotor speeds in these atmospheres. The self-electrophoresis mechanism of bisegment catalytic nanomotors suggests that the speed of such nanomotors is proportional to the $\Delta E_{Au/Pt}$ value.

We also considered the interfacial tension mechanism for the fuel-driven motion of Pt—Au nanowires. Briefly, oxygen produced on the Pt segment spreads by diffusion and disrupts the local interfacial tension between solid-liquid interface. This oxygen concentration remained constant over the Pt segment and varies gradually along the Au segment; leading to an interfacial tension gradient ($\Delta$ γ) along the nanomotor generating a net axial force that propels the wire. As expected, such interfacial tension gradient is influenced by the local oxygen level in the proximity of nanomotors and hence by the applied potential. Thus, at high oxygen levels (corresponding to a potential of +1.0 V), the gradient developed by peroxide decomposition on Pt segment is greatly reduced, leading to a decrease of nanomotor speed. Alternately, low oxygen levels (at the applied potential of −0.40 V) increase the gradient and hence the speed. The observed changes in the nanomotor speed (between 4 and 18 $\mu m\ s^{-1}$) are in good agreement with the theoretical calculations of Paxton et al for this model.

We also considered the possibility of oxygen poisoning of the catalytic activity of the platinum segment. While such poisoning can explain the data, it cannot account for the observed nanomotor behavior, as indicated from the reversible nature of the 'on/off' activation. Changes in the localized ionic strength and pH, associated with the electrochemical consumption or generation of protons, may also contribute to the magnitude of the axial force and hence influence the nanomotor motion. Finally, possible effects of silver or salt (leaking from the reference electrode) upon the motion were eliminated by placing the reference and counter electrodes away (~4 mm) from the working electrode and the plane of the measured nanomotors. The placement of the electrodes also leads to negligible electrostatic effects.

Various implementations have been described for an electrochemically-induced 'on/off' switching of the motion of catalytic nanomotors, along with a fine tuning of the motor speed through control of the applied potential. The potential-induced motion control is attributed primarily to changes in the local oxygen level in connection to the interfacial tension gradient. The ability to electrochemically trigger the motion of nanowire motors and to regulate their speed offers considerable promise for new challenging applications of these nanomotors.

Motion-based Biosensing of Cancer Biomarkers

In another aspect, described are techniques, apparatus and systems for implementing molecular recognition into the nanomotor movement for designing fundamentally new and powerful motion-based sensing strategy for improved cancer diagnostics and screening. The proposed use of motion for signal transduction represents new paradigm in bioanalysis as it relies on the speed and distance (traveled by nanomotors) to provide rich dimensions of analytical information. The attractive features of this new detection platform, include extremely high sensitivity, simplicity, speed, versatility, and low costs, and are expected to advance the early detection and treatment of cancer. As described in this document, biorecognition events of cancer markers can be converted into the nanomotor motion, based on different bimolecular interactions. These can include binding-triggered displacement/release and motion of an encoded tethered motor, tag-induced modulated movement, or use of functional nanomotors to isolate and separate disease markers or cancer cells. Quantitative milestones, set for these sensing protocols, can provide objective measures of the progress achieved throughout the project towards to specified goals. Alternative strategies can ensure compatibility of the requirements for the biomolecular interactions and nanomotor motion. The new motion-based sensing platform can lead to remarkable sensitivity, reflecting the ability to detect single-binding events via the binding-induced displacement/release of the nanomotors. The resulting distance signals could be easily recorded by optical microscope (without any sophisticated analytical instrument) to reveal the target presence and concentration.

For illustrative purposes, various embodiments are described, each corresponding to different motion transduction principles. For example, bioaffinity assays of cancer markers can be developed based on tag-induced modulated motion. The capture of an enzyme or nanoparticle tag can cause a dramatic change in the movement of nanomotors to offer convenient highly sensitive detection of the disease marker. Enzyme tags can lead to binding-induced modulation of the fuel level and hence to sharp speed changes.

In another example, displacement-based 'Signal On' Motion Sensing can be implemented. Novel displacement bioaffinity assays based on the ability of a target biomolecule to trigger the release and movement of an anchored nanomotor can be designed. Such motion-driven displacement assays can lead to a remarkable sensitivity, reflecting the ability to detect single binding event. Also described is selective capture and transport of disease markers. Strategies can be developed to include receptor-functional nanomotors, aimed at isolating and enriching protein disease markers or cancer cells. Antibody or aptamer-functionalized motors can be tested for transferring selectively the target biomarkers from complex blood environments into a pure buffer ideal for sensing. By providing remarkable sensitivity, great simplicity and low cost, and meeting the outlined milestones, the resulting motion-driven detection platform can be used to improve the efficiency of cancer diagnostics and therapy monitoring, and hence for increasing patient survival rates.

Early diagnosis of cancer is crucial for the successful treatment of the disease. Described techniques can be used to implement powerful new diagnostic tools for cancer screening based on the motion of artificial nanomotors. By delivering the diagnostic information in an extremely sensitive, yet simple and fast manner, such motion-driven bioassays can improve the efficiency of cancer diagnostics and therapy monitoring.

Protocols can be designed for transducing effectively the recognition of disease markers into motion and for using active transport for isolating and separating such markers. Such novel motion-based detection platform can lead to a dramatically amplified signal readout mechanism for ultra-sensitive cancer diagnostics based on the ability to detect single-binding events. The resulting distance signals could be easily recorded by optical microscope (without sophisticated instrumentation) to directly detect the biomarker recognition. Other important features of the new motion-driven detection platform can include high speed, versatility, low-cost and simplicity. Such attractive analytical features of the motion signal transduction can provide novel opportunities for cancer diagnostics that would significantly advance early detection of the disease, increase the chances of positive prognosis, lower treatment costs and would support the molecular detection of cancer, in general.

The proposed use of movement of artificial nanomotors for detecting cancer biomarkers represents a fundamentally new, novel and powerful biosensing strategy and a new paradigm in bioanalysis, in general. Such motion-driven signal transduction mechanism relies for the first time on measuring the distance signals, associated with the biorecognition-induced motion of nanomotors (see FIG. 9), for highly sensitive, yet simple, rapid and direct detection of cancer markers. The transduction of the molecular recognition events into the nanomotor movement can lead to a dramatically amplified signal readout mechanism for ultra-sensitive biodetection, including the ability to detect single binding events. Such innovative use of motion for signal transduction and marker separation can open up a new powerful dimension of information based on speed, distances, and active transport, and hence represents a major breakthrough in bioanalysis.

Synthetic nanomotors, converting chemical energy into autonomous motion can have various applications. The force, speed, efficiency, versatility, and motion control of catalytic nanomotors can be used to implement innovative biosensing strategy. In particular, the movement of artificial nanomotors can form the basis for developing a unique and powerful motion-based strategy for detecting and separating cancer markers.

Molecular recognition can be converted into the nanomotor movement for designing fundamentally new and powerful motion-based sensing strategy for improved cancer diagnostics, screening and therapy. The resulting motion-driven detection platform can provide new and rich dimensions of information based on distance and speed readouts, and will offer highly sensitive, rapid, simple and low cost detection of cancer biomarkers.

Techniques, apparatus and system are described for transducing biorecognition events of cancer biomarkers into the nanomotor motion. Single binding events could thus be readily detected via the recognition-induced displacement/release of the nanomotors to reveal the target presence. The resulting motion-based detection schemes can lead to highly-sensitive distance/speed readouts that are readily traced (measured) with an optical microscope.

Several motion-driven sensing protocols—based on different biomolecular interactions and motion transduction principles—can be designed and optimized. Alternative strategies can be explored for ensuring full compatibility of the requirements for the biomolecular interactions and nanomotor motion.

Develop Bioaffinity Assays of Cancer Markers Based on Tag-Induced Motion Switching.

Figure 25:
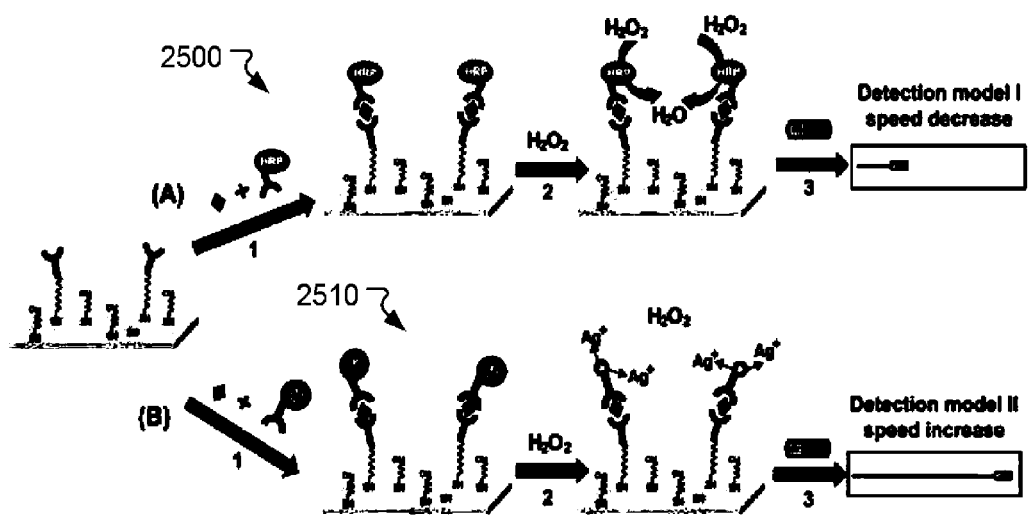
FIG. 25 shows motion immunoassays based on tag-induced modulated nanomotor movement. Sandwich assays based on capture of HRP (A) or Ag nanoparticle (B) tags and movement in a peroxide fuel.

Described are motion immunoassays of cancer biomarkers based on tag-induced switching of the motor speed. The capture of an enzyme or nanoparticle tag can cause a dramatic change in the movement of nanomotors to offer convenient highly-sensitive detection of the disease marker. FIG. 25 illustrates two such immunoassays of protein cancer markers involving motion acceleration in the presence of captured Ag nanoparticles tags (B, 2500) or suppressed speed in the presence of a fuel-consuming enzyme (HRP or catalase) tags (A, 2510). The nanoparticle-induced nanomotor acceleration reflects the dramatically enhanced speed of nanowire motors in the presence of silver ion. Alternately, consumption of the peroxide fuel and suppressed motion could be accomplished using common HRP or catalase tags (FIG. 25, A) or via 'artificial peroxidase' labels such as iron-oxide or Prussian Blue microparticles. The new tag-induced motion bioassays can undergo systematic optimization and critical evaluation. Proper attention will be given to the surface chemistry and receptor density in connection to mixed alkanethiol monolayers on gold surface. The overall performance ("figures of merit") and robustness of the new protocols can be examined under relevant conditions.

Figure 26:
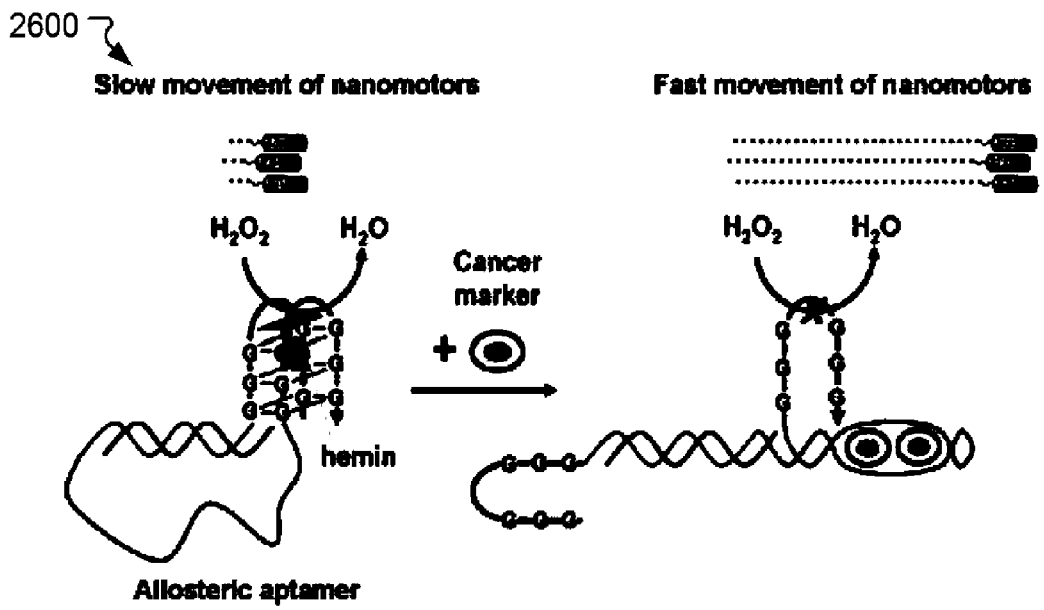
FIG. 26 shows motion-driven detection of cancer marker target based on allosteric aptamers with modulated peroxidase activity and hence fuel level.

Another 'smart' and attractive approach, described for highly specific and sensitive target detection, involves binding-induced changes in the peroxidase activity and hence in the fuel concentration. This can rely on allosteric aptamers in which one of the domains will possess peroxidase activity that will catalyze and consume the peroxide fuel so the nanomotor will stay inert (FIG. 26, Ref no. 2600). Binding of the cancer biomarker to the allosteric domain of the aptozyme can suppress the activity of the fuel-consuming peroxidase-active aptamer, hence inducing the nanomotor motion and revealing the presence of the target. Such target-controlled peroxidase activity forms the basis for the proposed sensing.

Demonstrate Displacement-Based Motion Sensing.

Figure 27:
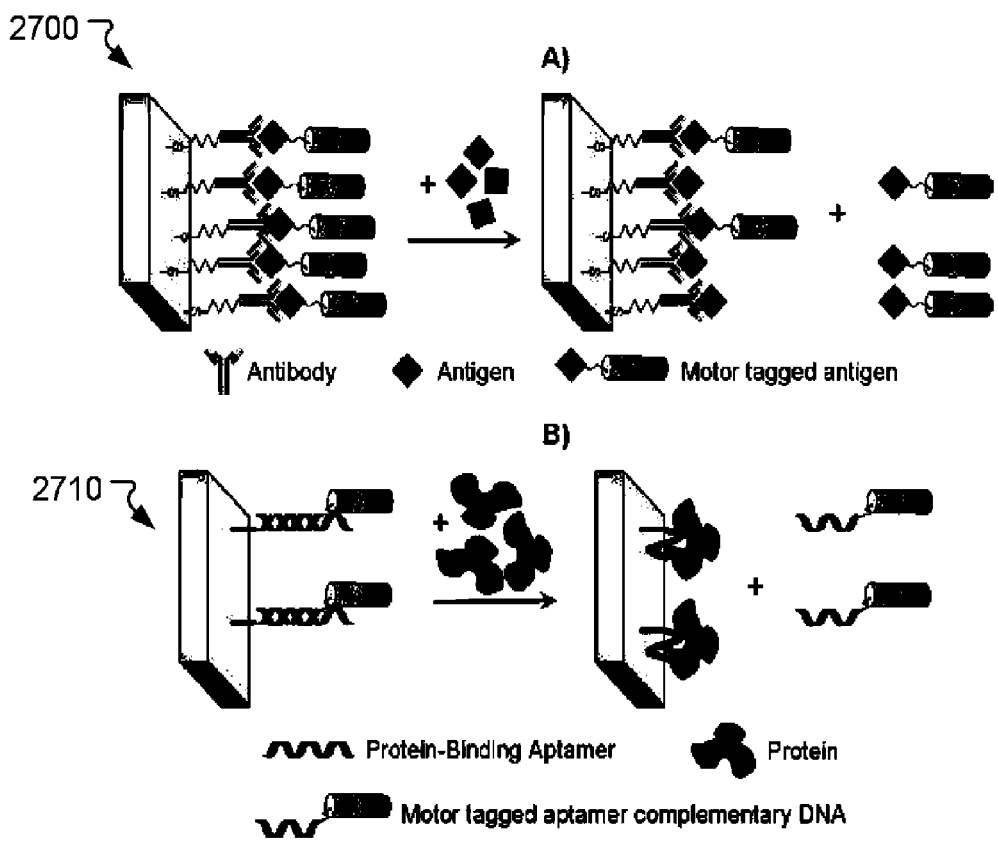
FIG. 27 shows Displacement-based motion sensing of protein biomarkers involving antibody (A) or aptamer (B) recognition. Binding of the target analyte will release the nanomotors from the surface-tethered receptor and initiate their movement.

Novel displacement bioaffinity assays are designed based on the ability of a target biomolecule to trigger the release and movement of a surface-tethered nanomotor (FIG. 27, Ref no. 2700 and 2710). Such reagentless binding-induced movement transduction ('Signal On' sensing) could lead to a dramatically amplified signal readout mechanism for ultrasensitive biodetection. Our ability to readily trace the movement of a single nanomotor indicates considerable promise for transducing and detecting single binding events. Unwanted background constituents are not expected to interfere (i.e., trigger such displacement). The ability of a target biomolecule to trigger the release and movement of a surface-bound nanomotor will be illustrated in connection to several biomolecular interactions of protein or nucleic acid targets. FIG. 27 illustrates two such displacement motion bioassays that we will develop and demonstrate using antibody (A, 2700) or aptamer (B, 2710) recognition of protein biomarkers. Binding of the target protein will lead to displacement and movement of the nanomotor 'tag' to reveal the target recognition (presence). The number of displaced motors will serve as the quantitative signal.

Variables involved in the new displacement motion bioassays can be systematically optimized. To ensure that the fuel and low-ionic strength requirements of the nanomotors will not affect the biomolecular interactions, the target biomarker (sample) will be added first followed by the low-ionic strength fuel solution. Using the aptamer displacements, low ionic strengths actually have a favorable effect upon the target binding. Alternately, salt-independent microtube 'rocket' can be used to ensure high compatibility of the binding and motion requirements. As common with displacement immunoassays, high displacement efficiency and hence sensitivity will be achieved by adjusting the binding strength through the use a sub-optimum (low-affinity) labeled antigen, e.g. PSA complex, displaced by the optimum high-affinity target antigen (the free PSA analyte).

Figure 28:
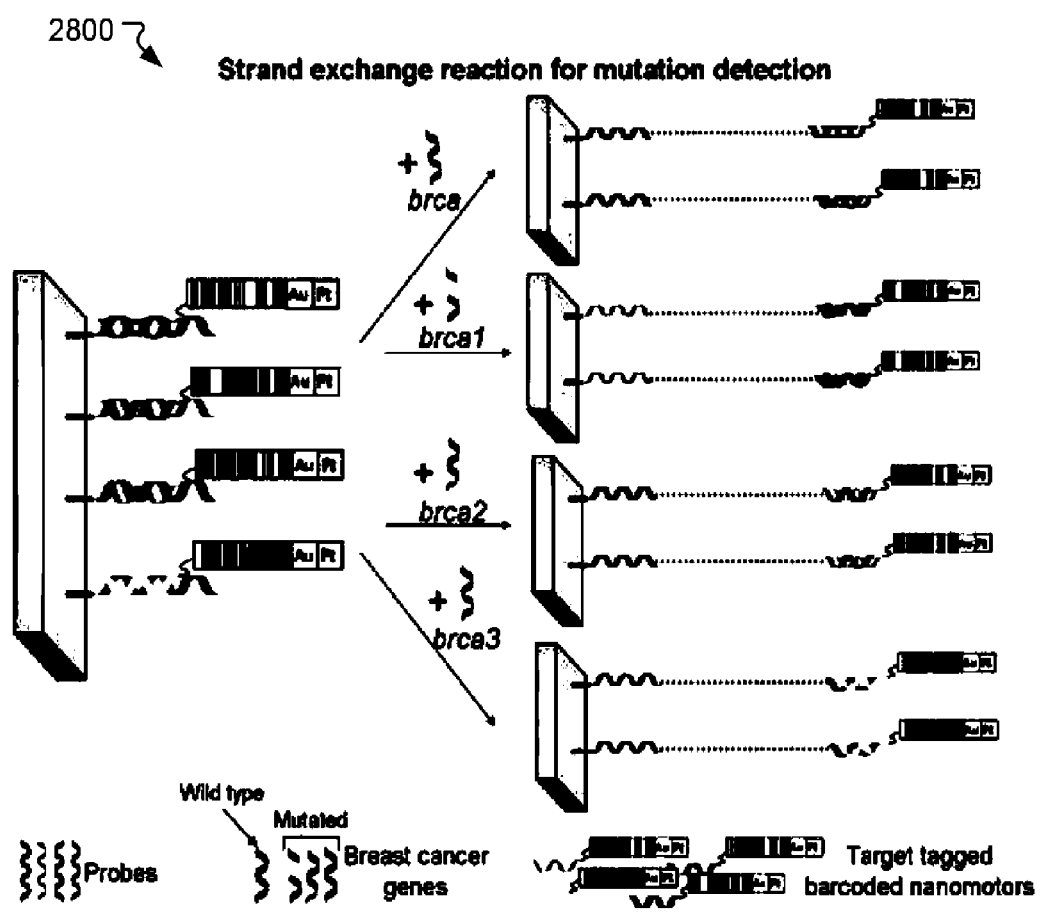
FIG. 28 shows multiplexed assay of breast-cancer mutated genes: Triggered motion of anchored barcoded nanomotors through analyte-induced strand exchange reaction and reflectivity identification of the displaced metal tags.

Based on the initial concept of displacement-based motion detection in connection to a single protein marker, simultaneous measurements of multiple disease markers can be implemented. Encoding the nanomotors with a multistripe Ag—Au barcode segment can provide for multiplexed motion bioassays (FIG. 28, ref no. 2800). The second route can involve multiple parallel microchannels containing (in their sample reservoir) the corresponding motor-tagged antigen attached to an immobilized antibody. In both cases, binding of the target analytes can induce the release and movement of the corresponding motors to allow simultaneous measurements multiple disease markers.

For example, FIG. 28 displays an exemplary multiplexed assay (2800) of breast-cancer related mutated genes involving the displacement of the corresponding barcoded nanomotors. The template nanowire preparation route can allow adding a barcoded Ag—Au multistripe section to the Pt—Au nanomotor, hence facilitating a rapid reflectivity identification. The motion-based multiplexed assay can be implemented using a strand exchange reaction between the nanomotor-tagged DNA and the target DNA. Upon the binding of the target to its specific probe, the corresponding DNA-functionalized encoded motor can be released to start moving around. The reflectivity readout, coupled with our microscopic detection, can allow convenient monitoring of the movement as well as identifying the specific oligotagged motor. Differences in the speed (induced by the Ag stripes) could also be exploited for distinguishing the individual signals.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

What is claimed is:

1. A system for detecting biomolecular interactions, comprising:
    a plurality of nanomachines, wherein each nanomachine of the plurality of nanomachines is to include two or more segments including a cathode segment and an anode segment, wherein at least one segment includes a functionalized surface, the nanomachine including a capture probe attached to the functionalized surface of the nanomachine, wherein the capture probe includes a region to molecularly bind to a target biological molecule;
    a fluid comprising a fuel substance and biomolecules including the target biological molecule, wherein the target biological molecule includes a complimentary region able to couple to the capture probe at the region of the capture probe;
    a nanoparticle assembly including a silver nanoparticle coupled to a molecular binding agent,
    wherein, when the nanomachines are present in the fluid, the capture probe is operable to form a complex with the nanoparticle assembly via the target biological molecule in the fluid on the nanomachine, and wherein the silver nanoparticle of the nanoparticle assembly catalyzes a reaction with the fuel substance to cause the nanomachine to autonomously move in the fluid; and
    an optical microscope to measure the motion of the nanomachine, wherein the complex formation of the capture probe with the nanoparticle assembly and the target biological molecule is indicated by the motion of the nanomachine,
    wherein the system is operable to detect binding of the target biological molecule to the capture probe and the nanoparticle assembly based on the motion of the nanomachine.

2. The system of claim 1, wherein the system is configured to detect a concentration of a plurality of target biological molecules based on a distance traveled by the nanomachine.

3. The system of claim 1, wherein the nanomachine is operable to move in the fluid based on the release of silver ions from the silver nanoparticle.

4. The system of claim 1, wherein the anode segment comprises platinum, and the cathode segment comprises gold.

5. The system of claim 1, wherein the target biological molecule comprises a nucleic acid.

6. The system of claim 1, wherein the target biological molecule comprises a cancer biomarker.

7. The system of claim 1, wherein the fuel substance includes hydrogen peroxide.

8. The system of claim 1, wherein the capture probe includes a single-stranded oligonucleotide, an aptamer, or an antibody.

9. The system of claim 1, wherein the surface of the at least one segment includes gold.

10. The system of claim 9, wherein the capture probe includes a thiol region attachable to the gold surface of the nanomachine.

11. The system of claim 9, wherein the functionalized surface includes mixed alkanethiol monolayers attached to the gold surface of the nanomachine.

12. The system of claim 9, wherein the functionalized surface includes a molecular monolayers complex, comprising: a dithiothreitol (DTT), and a 6-mercapto-1-hexanol (MCH).

13. The system of claim 1, wherein the nanomachine is operable to be steered by application of an external stimulus.

14. The system of claim 13, wherein the nanomachine is operable to be steered by application of an electromagnetic energy pulse as the external stimulus.

15. The system of claim 13, wherein the nanomachine is operable to be steered by application of a thermal energy pulse as the external stimulus.

16. The system of claim 13, wherein the nanomachine is operable to be steered by application of an electrochemical reaction in the fluid as the external stimulus.

17. The system of claim 1, wherein the motion of the nanomachine measured in the fluid corresponds to a concentration of the target biological molecule present in the fluid.

18. A system for detecting biomolecular interactions, comprising:
    a fuel substance;
    a nanomachine structured to include two or more segments including a cathode segment and an anode segment, wherein at least one segment includes a functionalized surface; and
    a complex formed on the nanomachine operable to bind to a biological target and drive autonomous motion of the nanomachine in a fluid containing the fuel substance, the complex including:
        a capture probe attached to the functionalized surface of the nanomachine, and
        a nanoparticle assembly including a silver nanoparticle and a molecular binding agent, the nanoparticle assembly coupled to the capture probe by the biological target, wherein the complex is structured to bind the biological target at a region of the capture probe having a molecular structure configured to molecularly couple to a complimentary molecular structure of the biological target, and wherein the complex is structured to drive the nanomachine by a reaction of the fuel substance with the nanomachine based on catalysis of the silver nanoparticle, wherein motion of the nanomachine measured in the fluid corresponds to a characteristic of the biological target present in the fluid.

19. A method for detecting biomolecular interactions based on nanomachine motility, the method comprising:

providing a fluid containing biomolecules including a biological target;

deploying, into the fluid:

a nanomachine structured to include two or more segments including a cathode segment and an anode segment, wherein at least one segment includes a functionalized surface, a capture probe attached to the functionalized surface of the nanomachine, the capture probe including a region having a molecular structure configured to molecularly couple to a complimentary molecular structure of the biological target, and a nanoparticle assembly including a silver nanoparticle and a molecular binding agent;

forming a complex on the nanomachine by coupling the nanoparticle assembly to the capture probe via the biological target;

adding a fuel substance to the fluid, wherein the complex on the nanomachine causes autonomous motion of the nanomachine based on a reaction of the fuel substance facilitated by catalysis of the silver nanoparticle in the fluid;

measuring, using an optical microscope, the motion of the nanomachine in the fluid; and determining a characteristic of the biological target based on the measured motion of the nanomachine.

* * * * *